United States Patent
Fleischer et al.

(10) Patent No.: US 8,427,650 B2
(45) Date of Patent: Apr. 23, 2013

(54) RECONSTRUCTION OF NONLINEAR WAVE PROPAGATION

(75) Inventors: Jason W. Fleischer, Princeton, NJ (US); Christopher Barsi, Yonkers, NY (US); Wenjie Wan, Princeton, NJ (US)

(73) Assignee: Opteryx, LLC, Princeton, NJ (US)

( * ) Notice: Subject to any disclaimer, the term of this patent is extended or adjusted under 35 U.S.C. 154(b) by 433 days.

(21) Appl. No.: 12/629,739

(22) Filed: Dec. 2, 2009

(65) Prior Publication Data

US 2010/0165348 A1 Jul. 1, 2010

Related U.S. Application Data

(60) Provisional application No. 61/200,671, filed on Dec. 2, 2008.

(51) Int. Cl.
*G01B 9/021* (2006.01)
*G01N 21/00* (2006.01)

(52) U.S. Cl.
USPC .......................................... 356/457; 356/73.1

(58) Field of Classification Search ................... 356/457, 356/73.1
See application file for complete search history.

(56) References Cited

U.S. PATENT DOCUMENTS

| | | | |
|---|---|---|---|
| 4,411,520 A * | 10/1983 | Mochizuki et al. | 356/73.1 |
| 4,796,992 A * | 1/1989 | Aoshima et al. | 356/457 |
| 4,960,332 A | 10/1990 | Foldi et al. | |
| 5,991,021 A * | 11/1999 | Mukherjee et al. | 356/317 |
| 7,199,882 B2 | 4/2007 | Svetkoff et al. | |
| 7,385,706 B2 * | 6/2008 | Dorrer | 356/477 |
| 7,417,742 B2 * | 8/2008 | Ozcan et al. | 356/511 |
| 7,424,191 B2 * | 9/2008 | Tadakuma et al. | 385/122 |
| 7,545,494 B2 * | 6/2009 | Haiml et al. | 356/317 |
| 7,869,014 B2 * | 1/2011 | Tadakuma et al. | 356/73.1 |
| 8,009,279 B2 * | 8/2011 | Hempstead | 356/73.1 |
| 2006/0111644 A1 | 5/2006 | Guttag et al. | |
| 2008/0001735 A1 | 1/2008 | Tran | |
| 2010/0020204 A1 * | 1/2010 | Fleischer et al. | 348/241 |
| 2010/0165328 A1 * | 7/2010 | Hirano et al. | 356/73.1 |

(Continued)

FOREIGN PATENT DOCUMENTS

WO WO 2010/065651 6/2010

OTHER PUBLICATIONS

Yariv, A., "Three-dimensional pictorial transmission in optical fibers," Appl. Phys. Let., vol. 28, No. 2, Jan. 15, 1976, pp. 88-89.

(Continued)

*Primary Examiner* — Hwa Lee
(74) *Attorney, Agent, or Firm* — Knobbe, Martens, Olson and Bear, LLP

(57) ABSTRACT

Disclosed are systems and methods for characterizing a nonlinear propagation environment by numerically propagating a measured output waveform resulting from a known input waveform. The numerical propagation reconstructs the input waveform, and in the process, the nonlinear environment is characterized. In certain embodiments, knowledge of the characterized nonlinear environment facilitates determination of an unknown input based on a measured output. Similarly, knowledge of the characterized nonlinear environment also facilitates formation of a desired output based on a configurable input. In both situations, the input thus characterized and the output thus obtained include features that would normally be lost in linear propagations. Such features can include evanescent waves and peripheral waves, such that an image thus obtained are inherently wide-angle, farfield form of microscopy.

59 Claims, 10 Drawing Sheets

U.S. PATENT DOCUMENTS

2010/0165348 A1* 7/2010 Fleischer et al. ............... 356/458
2010/0253936 A1* 10/2010 Xia et al. ...................... 356/73.1
2012/0069345 A1* 3/2012 Shaffer et al. ................. 356/457

OTHER PUBLICATIONS

Yariv, A., "Compensation for atmospheric degradation of optical beam transmission by nonlinear optical mixing," Optics Communications, vol. 21, No. 1, Apr. 1977, pp. 49-50.

Fischer B. et al., "Real-time phase conjugate window for one-way optical field imaging through a distortion," Appl. Phys. Lett 41(2), Jul. 15, 1982, pp. 141-143.

Khyzniak, V. et al., "Phase conjugation by degenerate forward four-wave mixing," J. Optical. Society of America, vol. 1, No. 2, Feb. 1984, pp. 169-175.

Jones, D.C., et al., "Three-wave and four-wave forward phase-conjugate imaging in photorefractive bismuth silicon oxide," Optical Society of America, Optics Letters, vol. 15, No. 17, Sep. 1, 1990, pp. 935-937.

Kip, D. et al., "Transmission of images through highly nonlinear media by gradient-index lenses formed by incoherent solitons," Optical Society of America, Optics Letters, vol. 26, No. 8, Apr. 15, 2001, pp. 524-526.

Schnars, U. et al., "Direct recording of holograms by a CCD target and numerical reconstruction," Applied Optics, vol. 33, No. 2, Jan. 10, 1994, pp. 179-181.

Schnars, U. et al., "Digital recording and numerical reconstruction of holograms," Institute of Physics Publishing, Measurement Science and Technology 13 (2002) pp. R85-R101.

Tsang, M. et al., "Reverse propagation of femtosecond pulses in optical fibers," Optical Society of America, Optics Letters, vol. 28, No. 20, Oct. 15, 2003, pp. 1873-1875.

Yamaguchi, I. et al., "Phase-shifting digital holography," Optical Society of America, Optics Letters, vol. 22, No. 16, Aug. 15, 1997, pp. 1268-1270.

Goldfarb, G. et al., "Demonstration of fibre impairment compensation using split-step infinite-impulse-response filtering method," Electronics Letters, vol. 44, No. 13, Jun. 19, 2008, in 2 Pages.

Mateo, E. et al., "Impact of XPM and FWM on the digital implementation of impairment compensation for WDM transmission using backward propagation," Optics Express, vol. 16, No. 20, Sep. 29, 2008, pp. 16124-16137.

Segev, M. et al., "Steady-State Spatial Screening Solitons in Photorefractive Materials with External Applied Field," The American Physical Society, Physical Review Letters, vol. 73, No. 24, Dec. 12, 1994, pp. 3211-3214.

Christodoulides, D.N. et al., "Bright, dark and gray spatial soliton state in photorefractive media," Optical Society of America, vol. 12, No. 9, Sep. 1995, pp. 1628-1633.

Wan, W. et al., "Dispersive superfluid-like shock waves in nonlinear optics," Articles, Published online: Dec. 17, 2006, Nature Physics, vol. 3, Jan. 2007, www.nature.com/naturephysics, pp. 46-51.

Ghofraniha, N. et al., "Shocks in Nonlocal Media," The American Physical Society, Physical Review Letters, 2007, pp. 043903-1-043903-4.

Shih, M. et al., "Two-dimensional steady-state photorefractive screening solitons," Optical Society of America, Optics Letters, vol. 21, No. 5, Mar. 1, 1996, pp. 324-326.

Linzon, Y. et al., "Near-field imaging of nonlinear pulse propagation in planar silica waveguides," The American Physical Society, Physical Review E 72, 2005, pp. 066607-1-066607-5.

Krokel, D. et al., "Dark-Pulse Propagation in Optical Fibers," The American Physical Society, Physical Review Letters, vol. 60, No. 1, Jan. 4, 1988, pp. 29-32.

Oppenheim A.V. et al., "The Importance of Phase in Signals," IEEE, vol. 69, No. 5, May 1981, pp. 529-550.

Agrawal, G.P., "Modulation Instability Induced by Cross-Phase Modulation," The American Physical Society, Physical Review Letters, vol. 59, No. 8, Aug. 24, 1987, pp. 880-883.

Stentz, A.J. et al., "Induced focusing and spatial wave breaking from cross-phase modulation in a self-defocusing medium," Optical Society of America, Optics Letters, vol. 17, No. 1, Jan. 1, 1992, pp. 19-21.

Hickmann, J.M. et al., "Observation of Spatial Cross-Phase Modulation Effects in a Self-Defocusing Nonlinear Medium," Physical Review Letters, vol. 68, No. 24, Jun. 15, 1992, pp. 3547-3550.

Jia, S. et al., "Forward four-wave mixing with defocusing nonlinearity," Optical Society of America, Optics Letters, vol. 32, No. 12, Jun. 15, 2007, pp. 1668-1670.

Tomlinson, W.J. et al., "Reflection of a Gaussian beam at a nonlinear interface," Optical Society of America, Applied Optcs, vol. 21, No. 11, Jun. 1, 1982, pp. 2041-2051.

Emile, O. et al., "Measurement of the Nonlinear Goos-Hanchen Effect for Gaussian Optical Beams," The American Physical Society, Physical Review Letters, vol. 75, No. 8, Aug. 21, 1995, pp. 1511-1513.

Jost, B.M. et al., "Observation of the Goos-Hanchen Effect in a Phase-Conjugate Mirror," The American Physical Society, Physical Review Letters, vol. 81, No. 11, Sep. 14, 1998, pp. 2233-2235.

Ash, E.A., et al., "Super-resolution Aperture Scanning Microscope," Nature Publishing Group, Nature, vol. 237, Jun. 30, 1972, pp. 510-512.

International Search Report in PCT/US2009/066429 (WO 2010/065651), dated Feb. 26, 2010.

Written Opinion of the International Search Authority in PCT/US2009/066429 (WO 2010/065651), dated Feb. 26, 2010.

International Preliminary Report on Patentability in PCT/US2009/066429 (WO 2010/065651), dated Jun. 7, 2011.

* cited by examiner

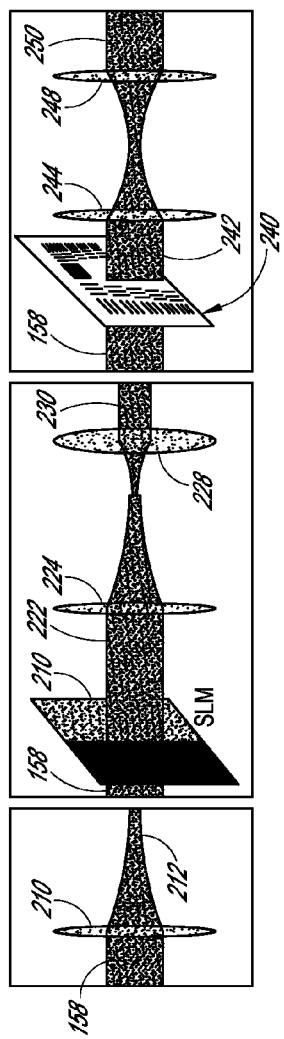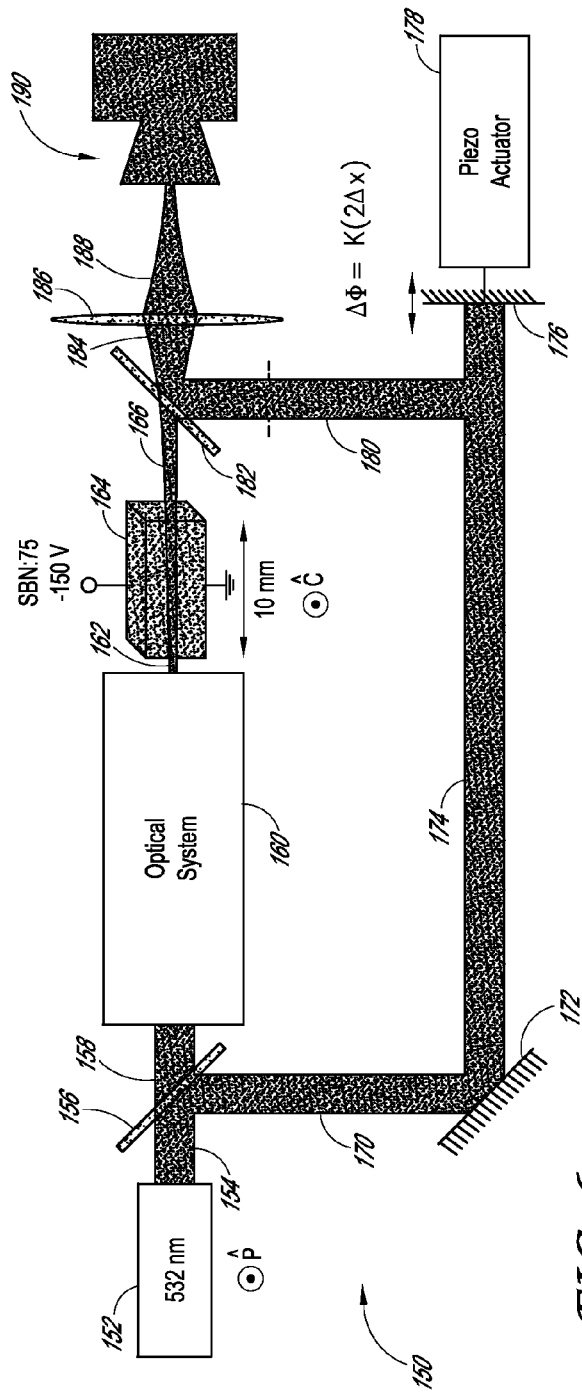

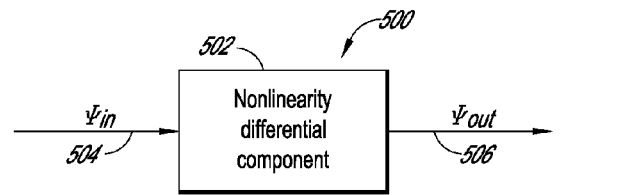
FIG. 17
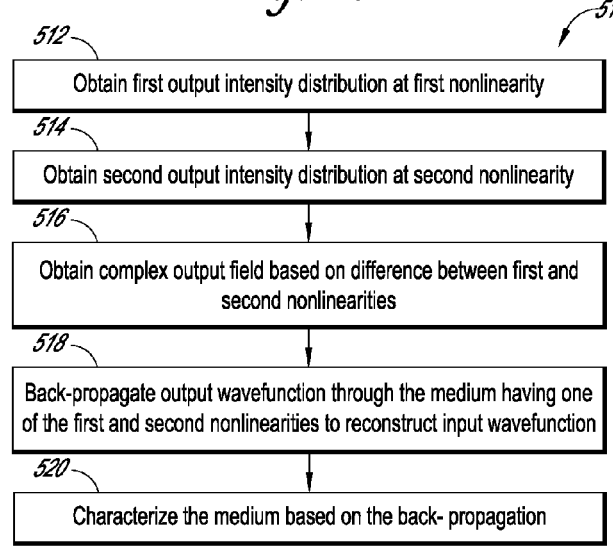
FIG. 18
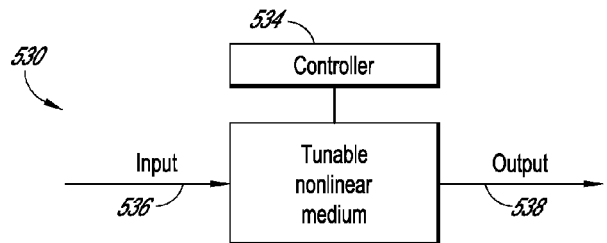
FIG. 19
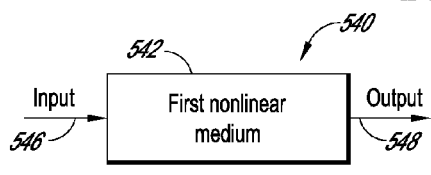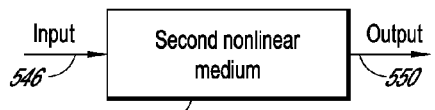
FIG. 20
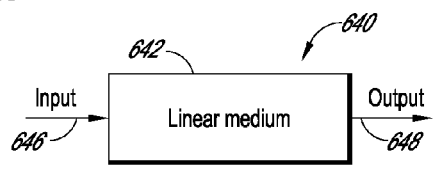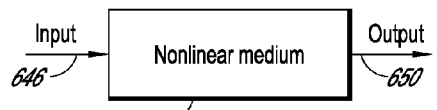
FIG. 21

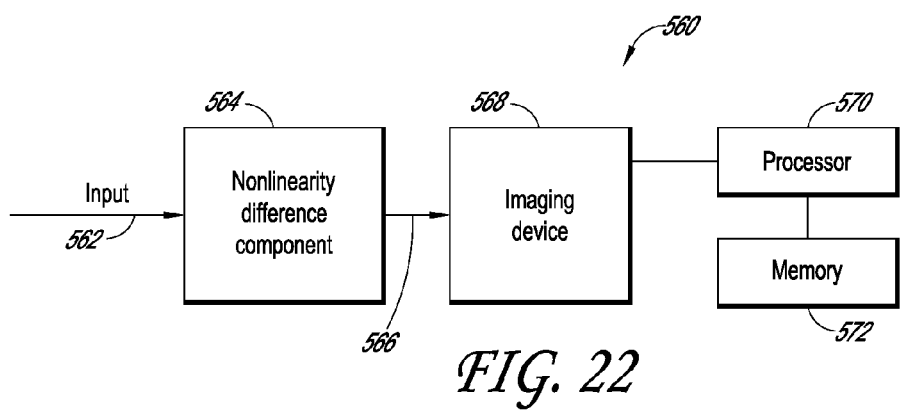
FIG. 22
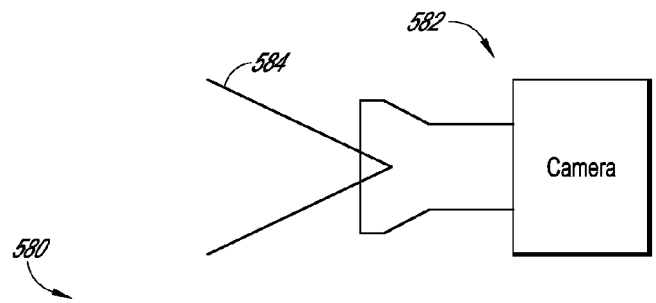
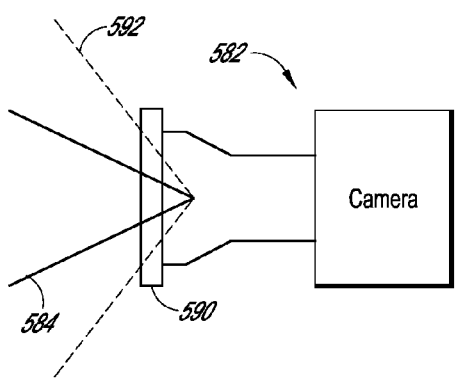
FIG. 23

RECONSTRUCTION OF NONLINEAR WAVE PROPAGATION

CROSS-REFERENCE TO RELATED APPLICATIONS

This application claims the benefit of priority under 35 U.S.C. §119(e) to U.S. Provisional Application No. 61/200,671, filed on Dec. 2, 2008, entitled, "HOLOGRAPHIC RECONSTRUCTION OF NONLINEAR WAVE PROPAGATION," the entirety of which is incorporated herein by reference.

STATEMENT REGARDING FEDERALLY SPONSORED R&D

This invention was made with Government support under Grant No. NSF PHY-0605976 awarded by the National Science Foundation; Grant No. AFOSR FA9550-07-1-0249 awarded by the Air Force Office of Scientific Research; Department of Defense grant awarded by the Army Research Office through a National Defense Science and Engineering Graduate Fellowship; and Grant No. DE-FG02-08ER55001 awarded by the Department of Energy. The Government has certain rights in this invention.

BACKGROUND

1. Field

The present disclosure generally relates to the field of nonlinear wave propagation, and more particularly, to systems and methods for modeling and/or calculation of optical wave propagation and uses thereof.

2. Description of the Related Art

Propagation of waves can occur in various media that can be classified into either a linear medium or a nonlinear medium. In a linear medium, dynamics are independent of wave intensity and wave propagation occurs such that superposition principle holds. In a nonlinear medium, the superposition principle does not hold. As generally known, this distinction is important because many physical systems can be modeled as linear systems. For physical systems that are generally approximately linear, linear modeling can provide an approximation of the true physical behavior. However, all media exhibit nonlinear behavior, if the wave energy is high enough.

In a nonlinear medium, a propagating wave may undergo intensity-dependent phase changes, thereby distorting signals as they propagate. In certain situations, such distortion of signals due to the nonlinear propagation is sometimes referred to as "wave mixing." Among other consequences, such wave mixing due to nonlinearity results in significant effects such as mode coupling, generation of new frequencies, and modifications to the signal phase.

SUMMARY

In certain embodiments, the present disclosure relates to a method for characterizing a nonlinear medium. The method includes providing a known input waveform to said nonlinear medium such that said input waveform propagates through said nonlinear medium. The input waveform is representative of two or more dimensional spatial information. The method further includes characterizing an output waveform emerging from said nonlinear medium. The method further includes computationally propagating said output waveform through said nonlinear medium so as to obtain an estimated waveform that sufficiently matches said input waveform. The computational propagation depends on one or more properties of said nonlinear medium such that obtaining of said estimated waveform results in characterization of said one or more properties of said nonlinear medium.

In certain embodiments, said nonlinear medium comprises a nonlinear optical medium. In certain embodiments, said characterizing of said output waveform comprises characterizing a complex field emerging from said nonlinear medium. In certain embodiments, an amplitude is measured directly by an imaging device, and a phase is measured holographically by interference measurement. In certain embodiments, said input waveform comprises a coherent waveform.

In certain embodiments, the method further includes measuring correlation among various components of said input waveform. In certain embodiments, said input waveform comprises an incoherent waveform.

In certain embodiments, said computationally propagating comprises numerically evaluating a nonlinear wave equation applied to a field representative of said output waveform. In certain embodiments, said field comprises a slowly-varying scalar field. In certain embodiments, said numerically evaluating comprises numerically evaluating backward propagation of said scalar field through said nonlinear medium. In certain embodiments, said backward propagation of said field is based on said field being estimated as $\Box(z_i) \approx e^{-dz \cdot N(\Box)} e^{-dz \cdot D} \Box(z_f = z_i + dz)$, where quantity z represents a propagation direction with $z_f > z_i$, quantity dz represents an incremental propagation distance, and quantities D and N represent linear and nonlinear operators, respectively.

In certain embodiments, the method further includes storing information about said one or more properties so as to allow retrieval and application to an unknown input waveform to characterize a resulting output waveform, or to a configurable input waveform that yields a desired output waveform.

In certain embodiments, the present disclosure relates to an optical system having a nonlinear optical medium configured to receive a first waveform and yield a second waveform. The system further includes a processor configured so as to obtain information about two of said nonlinear optical medium, first waveform, and second waveform and generate characterization of the remaining one of said nonlinear optical medium, first waveform, and second waveform. The generated characterization includes numerical propagation of one of said first and second waveforms through said nonlinear optical medium.

In certain embodiments, said processor is configured so as to obtain information about said first waveform and said second waveform and generate characterization of said nonlinear optical medium. In certain embodiments, said processor is configured so as to obtain information about said first waveform and said nonlinear optical medium and generate characterization of said second waveform. In certain embodiments, said second waveform comprises an output waveform emerging from said nonlinear optical medium. In certain embodiments, said output waveform includes one or more components originating from within said nonlinear optical medium as said first waveform propagates therethrough, such that when said output waveform is incident on a substrate, said one or more components interacts with said substrate. In certain embodiments, said one or more components are configured for use in lithography. In certain embodiments, said output waveform includes one or more components originating from within said nonlinear optical medium as said first waveform propagates therethrough. The one or more components have selected information attributable to said first waveform. In certain embodiments, said output waveform is configured for transmission to a remote location.

In certain embodiments, said second waveform comprises a waveform at least partially within said nonlinear optical medium. In certain embodiments, said second waveform includes one or more components originating from within said nonlinear optical medium as said first waveform propagates through at least a portion of said nonlinear optical medium, such that said one or more components interacts with said nonlinear optical medium in a desired manner. In certain embodiments, said nonlinear optical medium comprises a data storage medium.

In certain embodiments, said processor is configured so as to obtain information about said second waveform and said nonlinear optical medium and generate characterization of said first waveform. In certain embodiments, said first waveform comprises a first component and a second component, with said first and second components coupling in said nonlinear optical medium to generate a new nonlinear component that becomes part of said second waveform even if either or both of said first and second components of said first waveform to not become part of said second waveform. The new nonlinear component carries information imparted to it during said coupling. In certain embodiments, at least one of said first and second components of said first waveform comprises an evanescent wave component associated with an object being observed. In certain embodiments, said evanescent wave is associated with a subwavelength sized feature on said object. In certain embodiments, said object is in contact with said nonlinear optical medium so as to allow coupling of said evanescent wave component with one of said first and second components so as to yield said new nonlinear component. In certain embodiments, said nonlinear optical medium is part of a sample holder for holding said object. In certain embodiments, said sample holder comprises a microscope slide. In certain embodiments, said sample holder comprises an enclosure that encloses at least a portion of said object being imaged.

In certain embodiments, at least one of said first and second components of said first waveform comprises a peripheral component that would be lost and not become part of said second waveform if propagated through a linear optical medium. In certain embodiments, said information imparted by said peripheral component to said new nonlinear component increases effective field of view said first waveform captured by said second waveform. In certain embodiments, said nonlinear optical medium comprises a filter configured to be placed in front of an imaging device so as to provide said increased effective field of view. In certain embodiments, devices such as a profilometry device, a tomography device, or a material testing device can have features of the foregoing optical system. Such material testing device can be configured to characterize internal potentials of a material being tested, or to identify and characterize material defects or induced defects of a material being tested.

In certain embodiments, the present disclosure relates to a computer-readable medium containing machine-executable instructions that, if executed by a device having one or more processors, causes the device to perform operations. Such operations include obtaining a digital representation of a measured output waveform resulting from propagation of an input waveform through a nonlinear medium. The operations further include computationally propagating said digital representation of said measured output waveform through said nonlinear medium so as to reconstruct a digital representation of said input waveform, with said computational propagation depending on one or more properties of said nonlinear medium, information about said one or more properties stored in said computer-readable medium or accessible by said machine-executable instructions.

In certain embodiments, the present disclosure relates to a method for characterizing nonlinear wave propagation. The method includes providing a known input waveform to propagate through a first nonlinear environment so as to yield a first intensity distribution. The method further includes providing said known input waveform to propagate through a second nonlinear environment so as to yield a second intensity distribution. The method further includes determining an output waveform based at least in part on a difference between said first and second intensity distributions. The method further includes computationally propagating said output waveform through one of said first and second nonlinear environments to reconstruct an approximation of said input waveform.

In certain embodiments, the method further includes characterizing said one of said first and second nonlinear environments based on said computational propagation. In certain embodiments, the method further includes storing information representative of said characterization of said one of said first and second nonlinear environments in a computer-readable medium. In certain embodiments, said nonlinear wave propagation comprises nonlinear propagation of electromagnetic radiation.

In certain embodiments, the present disclosure relates to an optical system having a nonlinearity component configured to provide first and second nonlinear propagation environments for an input waveform to respectively yield first and second output waveforms. The system further includes an imaging device configured to detect at least intensity portions of said first and second output waveforms and generate first and second intensity distributions, respectively. The system further includes a processor configured to determine an output waveform based at least in part on a difference between said first and second intensity distributions.

In certain embodiments, said processor is further configured to computationally propagate said output waveform through one of said first and second nonlinear propagation environments to reconstruct an approximation of said input waveform. In certain embodiments, said nonlinearity component comprises a first medium and a second medium, said first medium providing said first nonlinear propagation environment and said second medium providing said second nonlinear propagation environment. In certain embodiments, one of said first and second environment comprises a propagation medium having a substantially zero degree of nonlinearity.

In certain embodiments, said nonlinearity component comprises a tunable nonlinear medium and a controller, where said controller is configured to provide at least two settings for said tunable nonlinear medium so as to provide said first and second nonlinear propagation environments. In certain embodiments, said output waveform includes phase information retrieved from said difference between said first and second intensity distributions. In certain embodiments, said output waveform includes polarization information retrieved from said difference between said first and second intensity distributions. In certain embodiments, said input waveform comprises incoherent wave, and wherein said output waveform includes correlation information to accommodate said incoherent wave.

In certain embodiments, the present disclosure relates to an apparatus having a nonlinear element configured so as to provide a nonlinear propagation environment for a wave passing therethrough, where said nonlinear element is dimensioned to receive an input and yield an output. The apparatus further includes a computer-readable medium containing instructions that calculates one of said input and output if given the other, said calculation achieved numerically in an iterative manner using one or more parameters that characterize said nonlinear propagation environment.

In certain embodiments, said apparatus comprises an imaging device. In certain embodiments, said instructions calculates said input based on said output. In certain embodiments, said output comprises a measured output. In certain embodiments, said apparatus comprises a microscope. In certain embodiments, said output comprises a desirable output. In certain embodiments, said apparatus comprises a lithographic device.

BRIEF DESCRIPTION OF THE DRAWINGS

FIG. 6 shows an example configuration for characterizing a nonlinear medium based on a known input and a measured output;

FIGS. 7A-7C show different example object inputs which can be used in the configuration of FIG. 6 to characterize the nonlinear medium and to verify the characterization;

FIG. 17 shows that in certain embodiments, various functionalities associated with characterization and use of characterized nonlinear media can be achieved by a nonlinearity differential component;

FIG. 18 shows that in certain embodiments, a process can be implemented to characterize a given nonlinear propagation based on a known input wavefunction and a difference between two measured output intensity distributions;

FIG. 19 shows an example of how two or more different nonlinear propagation environments can be provided;

FIG. 20 shows another example of how two or more different nonlinear propagation environments can be provided;

FIG. 21 shows an example where a linear propagation environment and a nonlinear propagation medium can be provided;

FIG. 22 shows that in certain embodiments, an imaging system can be configured to obtain an image of an object field via the nonlinearity difference component of FIG. 17;

FIG. 23 shows a more specific example of the imaging system of FIG. 22; and

These and other aspects, advantages, and novel features of the present teachings will become apparent upon reading the following detailed description and upon reference to the accompanying drawings. In the drawings, similar elements have similar reference numerals.

DETAILED DESCRIPTION OF CERTAIN EMBODIMENTS

The present disclosure generally relates to systems and methods for characterizing nonlinear wave propagation and solving for various unknowns in propagation of light through a nonlinear medium. As described herein, such characterization yields a number of practical applications, some of which can significantly extend performance capabilities in areas of optics technology.

Propagation of electromagnetic radiation can occur in various media that can be classified into either linear medium or nonlinear medium. In a linear medium, wave propagation occurs such that superposition principle holds. In a nonlinear medium, the superposition principle does not hold. As generally known, many physical systems can be modeled as linear systems. For physical systems that are generally approximately linear, linear modeling can provide an approximation of the true physical behavior.

In a nonlinear medium, a propagating wave may undergo intensity-dependent phase changes, thereby distorting signals as they propagate. In certain situations, distortion of signals due to the nonlinear propagation is sometimes referred to as "wave mixing." Among other consequences, such wave mixing due to nonlinearity results in significant effects such as mode coupling, generation of new frequencies, and modifications to the signal phase.

In the context of imaging, the dynamics of wave mixing within a nonlinear medium cannot be measured directly. In certain methods, all wave mixing occurring inside a nonlinear medium is inferred from profiles of the wave before entering the medium (initial) and exiting from the medium (final). Thus, in such methods, nonlinear wave dynamics are characterized by varying known input parameters and comparing measured outputs.

In the context of material characterization, some parameters of the nonlinear response of a medium can be inferred from comparison of known output with known input. For example, a thin nonlinear medium placed in the path of a focusing optical beam typically will change the properties of the focus, due to intensity-dependent changes to the phase. Moving the medium through the focus then allows successive measurements of the changes due to such parameters as the change in intensity, absorption, etc., as described in such papers as Sheik-Bahae, M., Said, A. A., & van Stryland, E. W., *High sensitivity single beam $n_2$ measurements*, Opt. Lett. 14, 955 (1989). For thick media, it is normally assumed that significant changes in beam shape do not occur. In various methods as described herein, physical scanning or beam refocusing is generally not needed and a greater degree of beam changes, wave mixing, etc., are allowed. Further, forward- and back-propagation techniques can be used to computationally recover material parameters.

Figure 1:
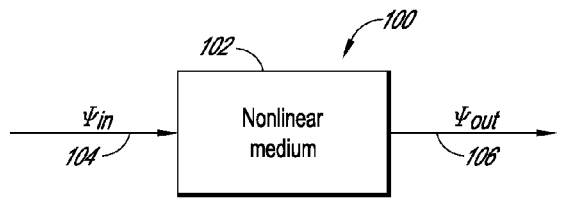
FIG. 1 schematically depicts a system having a nonlinear medium through which an input wavefunction propagates to yield an output wavefunction.

Provided herein are, among others, systems having a nonlinear medium, characterizing wave propagation within such a medium, and utilizing such characterization in various practical applications. In FIG. 1, such a system 100 is depicted as having a nonlinear medium 102 into which an input wave 104 (represented by a wavefunction $\psi_{in}$) is introduced. The input wave 104 propagates through the medium 102 and emerges from the medium 102 as an output wave 106 (represented by a wavefunction $\psi_{out}$).

Figure 2:
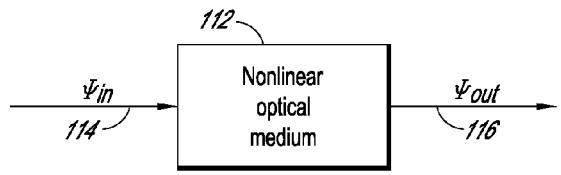
FIG. 2 shows that in certain embodiments, the nonlinear medium of FIG. 1 can be an optical medium having nonlinearity.

In certain embodiments, as shown in FIG. 2, the nonlinear medium can be a nonlinear optical medium 112 suitable for receiving an optical input wave 114 and generating an optical output wave 116. For the purpose of description herein, various nonlinear media and wave propagations therein are discussed in optics context. It will be understood, however, that one or more features of the present disclosure can be applied to nonlinear systems involving waves outside of what is typically considered to be optical regime.

In certain embodiments, the present disclosure relates to methods for characterizing a nonlinear medium. In certain embodiments, such characterization of the nonlinear medium includes using a nonlinear propagation model to back-propagate a measured output wave through the nonlinear medium to obtain a modeled input wave that is acceptably close to the known input wave.

Figure 3:
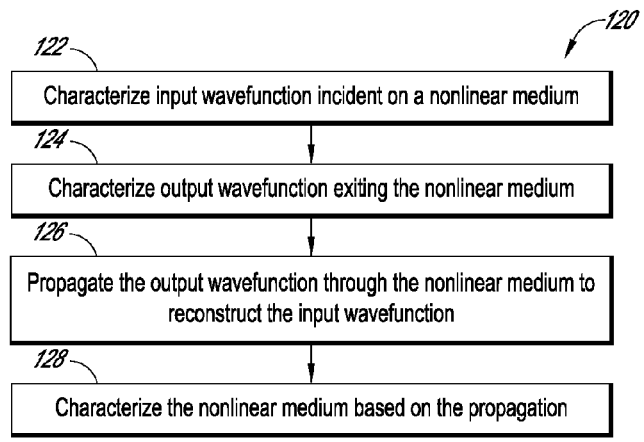
FIG. 3 shows that in certain embodiments, a process can be implemented to characterize a given nonlinear medium based on a known input wavefunction and a measured output wavefunction.

In certain embodiments, such characterization of the nonlinear medium can be implemented as a process 120 shown in FIG. 3. In a process block 122, an input wave incident on the nonlinear medium can be characterized. For example, a wavefunction of the input wave can be characterized. In certain embodiments, such characterization can include measurement of the input wave prior to entry into the nonlinear medium. In a process block 124, an output wave exiting from the nonlinear medium can be measured so as to yield an output wavefunction. In a process block 126, the output wavefunction can be numerically back-propagated through the nonlinear medium so as to substantially reconstruct the input wavefunction. Because the input wavefunction is known (in process block 122), accuracy of the numerical back-propagation methodology, and thus characterization of the nonlinear model of the medium, can be determined. Thus, in a process block 128, the nonlinear medium can be characterized based on the numerical back-propagation. In certain embodiments, such characterization can include an iterative process to obtain an estimation of one or more parameters associated with the nonlinear medium. In certain embodiments, such characterization can include a plurality of calculations of a wavefunction at various incremental positions within the nonlinear medium.

Figure 4:
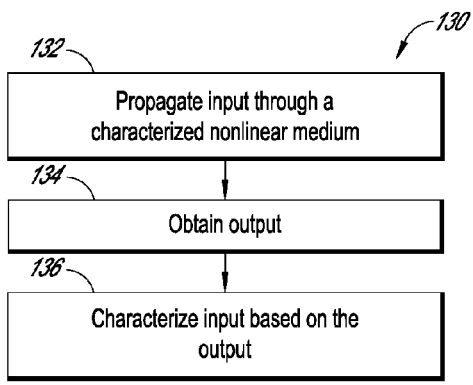
FIG. 4 shows that in certain embodiments, a process can be implemented to characterize an unknown input wavefunction based on a characterized nonlinear medium and a measured output wavefunction.

Once characterization of the nonlinear medium is obtained, an unknown input can be characterized based on a corresponding output that is either known or measured. Also, an input can be configured such that its propagation through the characterized nonlinear medium results in a desired output. FIG. 4 shows a process 130 that can be implemented to achieve the former; and FIG. 5 shows a process 140 that can be implemented to achieve the latter.

In certain embodiments, as shown in the process 130 of FIG. 4, an input that is either unknown or to be further characterized can be propagated in a process block through a nonlinear medium that has been characterized. In a process block 134, an output resulting from the nonlinear propagation can be obtained. In a process block 136, the input can be characterized based on the output and information representative of the characterized nonlinear medium. For example, a measured output can be numerically back-propagated through the nonlinear medium so as to obtain an estimation of the input.

Figure 5:
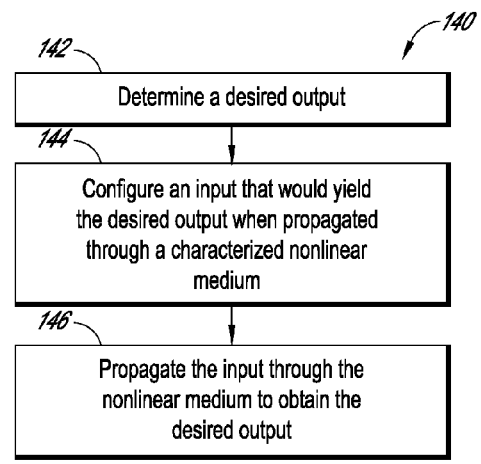
FIG. 5 shows that in certain embodiments, a process can be implemented to obtain a desired output wavefunction based on a characterized nonlinear medium and a configurable input wavefunction.

In certain embodiments, as shown in the process 140 of FIG. 5, a desired output can be determined in a process block 142. In a process block 144, an input can be configured such that propagation of the input through a characterized nonlinear medium yields an output that is acceptably close to the desired output. For example, an input can be calculated using calculation or back-propagation of the desired output through the medium. In certain embodiments, the actual output emerging from the nonlinear medium can be substantially same as the desired output. In a process block 146, the configured input can be propagated through the nonlinear medium to obtain an output that is an approximation of or substantially same as the desired output.

FIG. 6 shows an example setup 150 that can be utilized to facilitate characterization of a nonlinear medium 164. The setup includes a laser 152 that outputs a beam 154. The example laser 152 is a Verdi™ type laser operating at a wavelength λ of approximately 532 nm. The beam 154 is split by a beamsplitter 156 into first and second beams 158 and 170. The second beam 170 is used for phase measurement as described below. The first beam 158 is subjected to an optical system 160 that generates an object signal 162, and the object signal 162 from the optical system 160 acts as an input wave for the nonlinear medium 164. The input wave 162 can be represented by the wavefunction $\psi_{in}$ described herein.

The example nonlinear medium 164 is a photorefractive strontium barium niobate (SBN:75) crystal with a self-defocusing nonlinearity. The crystal 164 has transverse dimensions of approximately 2 mm×5 mm, and a longitudinal dimension of approximately 10 mm (along the propagation direction). The crystal 164 is oriented so that its crystalline c-axis (depicted as ĉ) is pointing in the substantially same direction as the polarization of the laser beam 154. Accordingly, the input wave 162 is extraordinarily polarized with respect to the crystal 164. To induce the nonlinearity property, the example crystal 164 is subjected to a voltage difference of approximately 150 V so as to yield an electric field of approximately −750 V/cm along the crystalline axis. To yield a substantially linear response of the crystal 164, the voltage to the crystal 164 is turned off. Also, the example crystal 164 can be rotated so that the 5 mm dimension is along the longitudinal direction. Thus, application or absence of voltage to the rotated crystal 164 yields nonlinear or linear propagation distance of 5 mm.

It will be understood that other types of nonlinear media can be used.

The input wave 162 is shown to propagate through the nonlinear medium 164 and emerge as an output wave 166. The output wave 166 is combined with a phase-shifted reference beam 180 by a beamsplitter 182 to yield a combined beam 184. As shown, the phase-shifted reference beam 180 is based on the second beam 170. The second beam 170 is redirected to a phase-shifting mirror 176 via a mirror 172. To shift the reference beam (170) into the phase-shifted reference beam (180), the phase-shifting mirror 176 is moved in incremental steps of approximately $\lambda/4$ via a piezo-actuator 178. In certain embodiments, such shifted images can allow removal of various artifacts from the interference terms, as described in, for example, Yamaguchi, I. & Zhang, T., *Phase-shifting digital holography*, Opt. Lett. 22, 1268 (1997).

As shown in FIG. 6, the combined beam 184 is imaged by an imaging device 190. As is generally known, a given combined beam 184 yields interference fringes in the corresponding image. The mirror 176 can be moved (e.g., to four locations) so as to yield different interference fringe patterns. Such fringe patterns can be analyzed by known algorithms to produce wavefront shapes.

In the example shown, the combined beam 184 is magnified approximately four times by a lens 186, and the magnified beam is imaged by a charge-coupled-device (CCD) having 520×492 array of 9.9 μm sized pixels. Such magnification allows one to better resolve various features of the field associated with the combined beam 184. Although the imaging lens 186 itself gives rise to a quadratic phase factor, because both reference (180) and object (166) beams are imaged together, no extraneous fringes in the interference pattern are produced.

An image of the combined beam 184 captured in the foregoing manner is a holographic representation of the output wave 166 emerging from the nonlinear medium 164. This digital holographic system produced phase information by optical interference holographic technique. Amplitude information can also be provided simply by detection of the beam propagated through the nonlinear medium 164 to the detector 190; and phase information can be obtained as described herein. Accordingly, the captured image includes information (amplitude and phase) representative of a full complex field.

In certain embodiments, propagation of the complex field representative of the output wave can be approximated as a scalar field undergoing paraxial dynamics, where a wavefunction $\psi(x,y,z)$ is a slowly varying envelope of the field. In this approximation, the propagation can be described by a nonlinear form of Schrödinger equation:

$$\frac{\partial \psi}{\partial z} = \left[i\frac{1}{2k}\nabla_\perp^2 + i\Delta n(|\psi|^2)\right]\psi \equiv [D + N(|\psi|^2)]\psi \quad \text{(Eq. 1)}$$

where $k=2\pi n_0/\lambda$, $\lambda$ is the free-space wavelength, $n_0$ is the medium's base index, $\Delta n(|\psi|^2)$ is the nonlinear index change, and D and N are the linear and nonlinear operators, respectively. A typical choice for $\Delta n(|\psi|^2)$ is the cubic Kerr nonlinearity, with $\Delta n=\gamma|\psi|^2$ where $\gamma$ is the nonlinear coefficient. For any nonlinearity, various issues generally can be considered. Such issues can include invertibility, integrability, vector decoupling, noise, nonlinear instabilities, and so on.

A wavefunction that satisfies Equation 1 and whose evolution can be calculated numerically using a known Fourier split-step method (in which the linear and nonlinear operators act individually for each increment of propagation distance dz), can be represented as:

$$\psi(z+dz) \approx e^{dz \cdot D} e^{dz \cdot N(\psi)} \psi(z). \quad \text{(Eq. 2)}$$

Equation 2 can be inverted by applying $e^{-dz \cdot N} e^{-dz \cdot D}$ to both sides to allow calculation of the field at some location $z_i$ given the field farther along the sample at location $z_f$ that is greater than $z_i$. Such inverted equation can be represented as:

$$\psi(z_i) \approx e^{-dz \cdot N(\psi)} e^{-dz \cdot D} \psi(z_f = z_i + dz). \quad \text{(Eq. 3)}$$

This back-propagation can be treated as an initial-value problem, in which the output is treated as a starting point. Such back-propagation works in situations where inverse scattering may fail, such as in media with non-integradble nonlinearities.

In certain embodiments, linear and nonlinear propagators ($e^{-dz \cdot D}$) and $e^{-dz \cdot N(\psi)}$, respectively) can be transformed into Fourier representations for the above-referenced numerical calculation via the known Fourier split-step method. The linear propagator's Fourier representation can be expressed as in Equation 4. Similarly, the nonlinear propagator can be represented as a Fourier transform of $e^{-dz \cdot \Delta n}$, where $\Delta n$ can be selected as described herein.

As is known, the method of back-propagating to overcome certain issues associated with nonlinear media was demonstrated for one-dimensional pulses in fiber. Additional details concerning such one-dimensional technique can be found in, for example, articles by Goldfarb, G. & Li, G., *Demonstration of fiber impairment compensation using split-step infinite-impulse-response filtering method*, Electron. Lett. 44, 814-81.5 (2008); and Mateo, E., Zhu, L. & Li, G., *Impact of XPM and FWM on the digital implementation of impairment compensation for WDM transmission using backward propagation*, Opt. Express 16, 16124-16137 (2008). It will be emphasized that application of this technique, as described herein, to two or more dimensional spatial beams containing image information adds considerable complexity to the inversion, for example, by introducing degenerate solutions or an anisotropic response. In certain situations, the increase in dimension can also add significant new consequences. For example, it is known that one typically cannot image through an optical fiber, as modes separate and distort as they propagate, as described in such papers as Yariv, A., *Three-dimensional pictorial transmission in optical fibers*, Appl. Phys. Lett. 28, 88 (1976).

For the example nonlinear medium 164 (SBN:75) of FIG. 6, the photorefractive screening nonlinearity of the crystal is saturable, with a response $$\Delta n \propto \frac{r_{ij} I}{1 + I},$$

where I is the intensity $I=|\psi|^2$, normalized to a background (dark current) intensity, and $r_{ij}$ is the appropriate electro-optic coefficient. However, recent experiments have shown that for the defocusing parameters considered here, the simpler Kerr nonlinearity $\Delta n=-|\gamma|I$ proves sufficient for modeling. Additional details concerning such approximation can be found at, for example, an article by Wan, W., Jia, S. & Fleischer, J. W., *Dispersive, superfluid-like shock waves in nonlinear optics*, Nature Phys. 3, 46-51 (2007). Similarly, loss has been ignored, although the inclusion of linear operators such as absorption should not affect or substantially affect the reconstruction process.

The uniaxial nature of the crystal 164 (SBN:75) introduces a slight anisotropy in the nonlinear response. To account for such anisotropy, a relatively small anisotropic correction (δ) of approximately 7% is introduced to the index of refraction in the x-direction for the linear propagator. Thus, in a Fourier domain representation, following correction can be introduced:

$$e^{-i\frac{\lambda \Delta z}{4\pi}\left(\frac{k_x^2}{n_0}+\frac{k_y^2}{n_0}\right)} \to e^{-i\frac{\lambda \Delta z}{4\pi}\left(\frac{k_x^2}{n_0(1+\delta)}+\frac{k_y^2}{n_0}\right)} \quad \text{(Eq. 4)}$$

where $\delta=0.07$ and $k_x$ and $k_y$ are the wavevectors for the x- and y-axis. The parameter δ can be held constant, although functional dependence on the intensity did not change the result. The value of δ does, however, can depend on the applied voltage. In the context of a Gaussian beam, this numerical approximation affects the Gaussian beam (as describe herein) generally at its focus only. Furthermore, it does not affect or substantially affect the other reconstructions as described herein. Therefore, it is believed that this modification becomes applicable to high-intensity, focused beams. If based on the foregoing anisotropic correction, other more complex models of the photorefractive nonlinearity that include charge transport and saturation effects may not be as successful at recovering the input.

In the example setup 150 of FIG. 6, the optical system 160 includes different configurations for providing different inputs to the nonlinear medium 164. In certain embodiments, a laser beam having a substantially Gaussian beam profile can be provided to the nonlinear medium to calibrate the foregoing back-propagation algorithm, thereby characterizing the nonlinear medium.

Figures 8A, 8B:
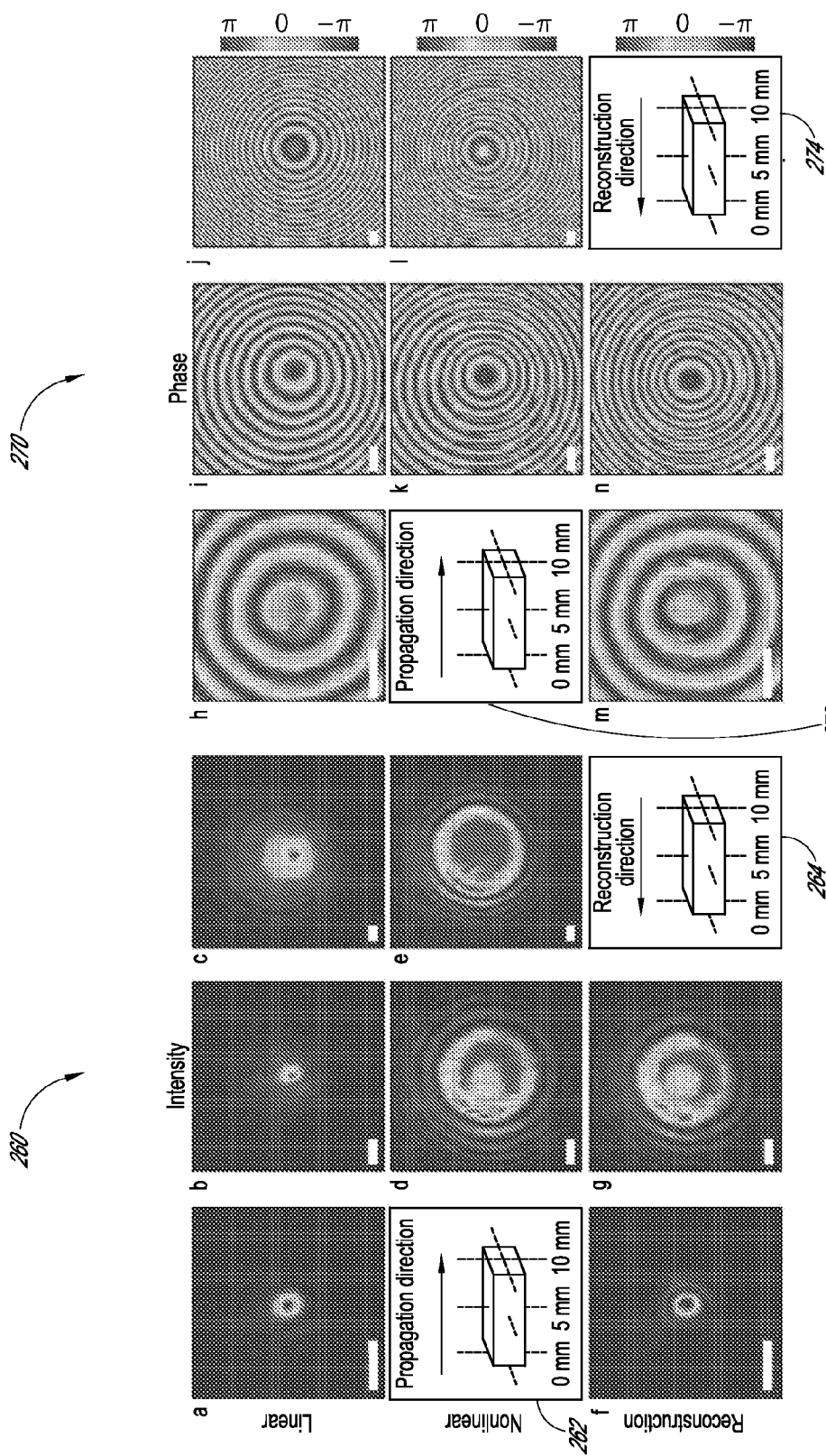
FIGS. 8A and 8B shows intensity and phase distributions of the input, measured linear propagation outputs, measured nonlinear propagation outputs, and back-propagation results for a Gaussian object beam input.

As shown in FIG. 7A, the back-propagation algorithm can be calibrated by focusing, via a lens 210 (e.g., a 20 cm planoconvex lens), a Gaussian beam 158 (approximately 10 μW) onto the input face of the crystal 164. FIGS. 8A and 8B show various panels (260, 270) at various stages of evolution of the Gaussian beam in linear propagation, nonlinear propagation, and numerical back-propagation.

In FIG. 8A, upper row of panels (a, b, c) show measured beam intensities for linear propagation (voltage turned off), at z=0 (input face of the crystal), z=5 mm (midpoint of the crystal, approximated by rotating the crystal), and z=10 mm (exit face of the crystal). Such locations are depicted in a panel indicated as 262. In FIG. 8B, upper row of panels (h, i, j) show measured phase measurements (modulo 2π) for linear propagation (voltage turned off), at z=0 (input face of the crystal), z=5 mm (midpoint of the crystal, approximated by rotating the crystal), and z=10 mm (exit face of the crystal). Such locations are depicted in a panel indicated as 272. In each of the panels a, b, c, h, i, and j, a scale bar representative of approximately 50 μm is provided at lower left corner.

Measured intensities and phases of nonlinear propagation are shown in middle rows of panels (d and e in FIG. 8A, and k and l in FIG. 8B). Panels d and k represent intensity and phase measurements at z=5 mm, respectively, obtained by measurements at the exit face of a similar crystal having a length of approximately 5 mm (in place of the 10 mm crystal). Panels e and l represent intensity and phase measurements at z=10 mm, respectively, obtained by measurements at the exit face of the 10 mm crystal. In each of the panels d, e, k, and l, a scale bar representative of approximately 50 μm is provided at lower left corner.

One can see the dramatically different output in the nonlinear case, particularly after 10 mm of propagation (roughly three diffraction lengths). In particular, the nonlinear beam has a depleted central region and high-frequency fringes at the edges, a profile that does occur in the linear case (in which a Gaussian beam stays Gaussian). These features can result from wavebreaking of the central portion of the beam into its own tails and are similar to the optical shocks demonstrated in articles such as Wan, W., Jia, S. & Fleischer, J. W., *Dispersive, superfluid-like shock waves in nonlinear optics*, Nature Phys. 3, 46-51 (2007).

The measured output field depicted in panels e and l of FIGS. 8A and 8B can be back-propagated numerically as described herein to reconstruct the measured input (panels f and m), as well as the midpoint (z=5 mm) field (panels g and n). As described herein in reference to FIG. 6, the imaging device 190 used for measurements of various fields has a CCD having 520×492 array of pixels. For the digital reconstruction, the frames recorded by the camera (190) were cropped horizontally, and padded with zeros vertically to create 512×512 pixel frames. In certain embodiments, the beam propagation code used optimally utilizes the fast Fourier transform (FFT) algorithm in linear step(s). The numerical pixel size was matched with the effective (demagnified) camera pixel size, 2.5 μm, and the propagation step size (Δz) was approximately 65 μm for the numerical back-propagation calculation. A decrease in the step size (Δz) to approximately 20 μm showed no appreciable change in the reconstruction, confirming that numerical convergence had been achieved.

To achieve the reconstructed input shown in panels f and m, the nonlinear coefficient γ is adjusted until the sum-of-squares error between the two profiles is substantially reduced or minimized. As shown panels f and m, there is very good agreement in both phase and intensity with the measured input (panels a and h). Similarly, and as shown panels g and n, there is very good agreement in both phase and intensity of the reconstruction at z=5 mm with the measured input counterparts (panels d and k). The agreement is particularly pronounced in the asymmetry of the central portion of the beam, which is slightly left of center.

In certain embodiments, a value of the nonlinear coefficient that yields the foregoing reconstruction can then be fixed and used for some or all subsequent measurements involving the crystal and different inputs.

Although the expanding Gaussian beam experiences significant changes in both intensity and phase, other nonlinear features or structures, such as solitons, generally maintain constant-intensity profiles and acquire only an overall phase change upon propagation. Normally, experimental observations of these structures follow from launching a beam close to the initial soliton profile; confirmation is then reported by comparing the original input to the nonlinear output after several diffraction lengths. Such an observation method, however, may say little about evolution towards a steady-state profile, especially for initial conditions far from the soliton existence curve. As is known, cut-back methods provide volumetric information but involve crystal damage or special geometry. Other methods, such as near-field probes and scattered-light measurements, are similarly direct but work well primarily for one-dimensional solitons and cross-sections.

In contrast, one or more features of the technique disclosed herein allow reconstruction, and thus effective imaging, of the beam dynamics all along its propagation, without relying on coupling mechanisms or material modification.

As shown in FIGS. 6 and 7B, the back-propagation algorithm calibrated as described herein can be used to reconstruct an image of a dark stripe pattern 220. As shown, the laser beam 158 passes through a spatial light modulator (SLM) or phase step 220 producing a π-stripe (black, 0 rad; grey, π rad) pattern in the transmitted beam 222. The beam 222 having phase discontinuity is imaged and demagnified approximately eight times with a 4f system (224, 228) so as to yield an object beam 230 (162 in FIG. 6) to be propagated through the nonlinear medium 162 (FIG. 6). Reconstruction of the input based on the measured output is performed similarly as in the Gaussian case, by formatting the frames recorded by the camera (190) into 512×512 pixel frames.

Figure 9:
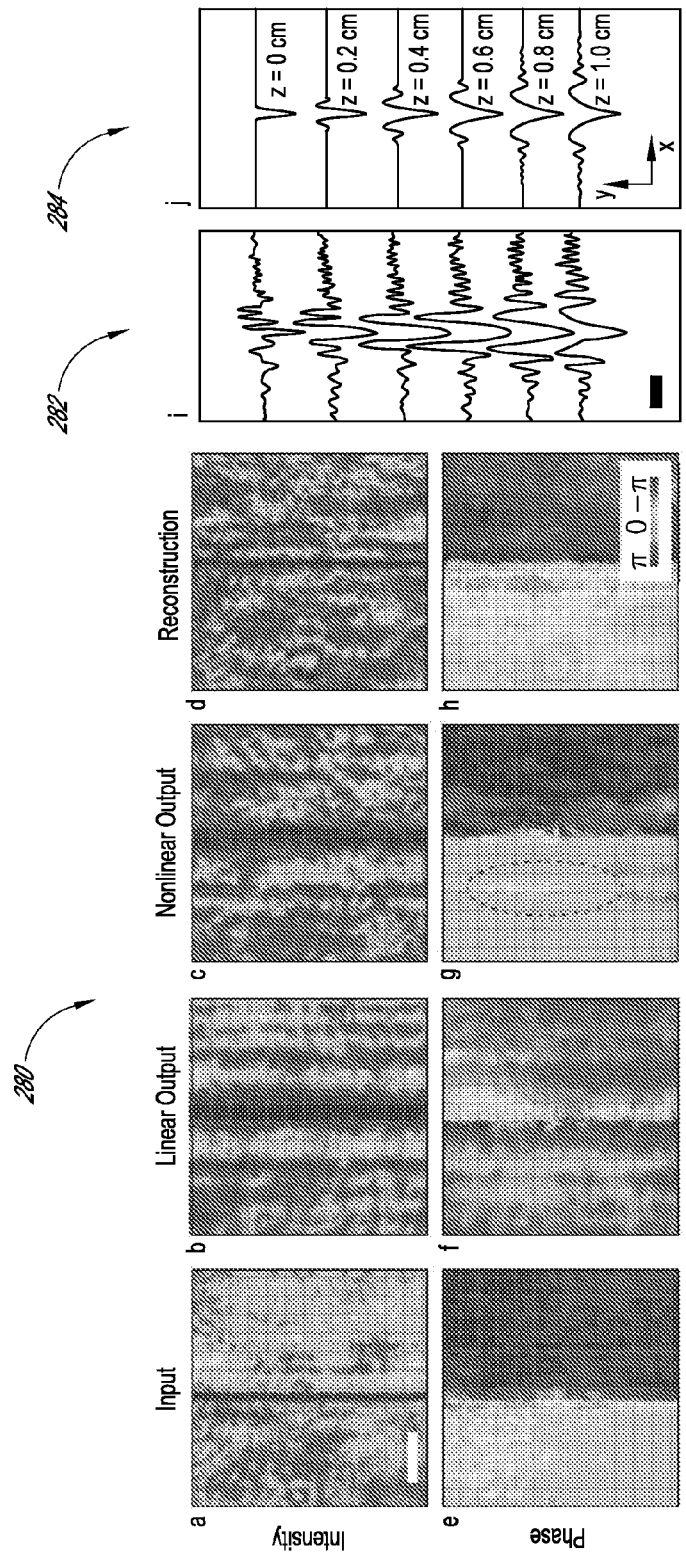
FIG. 9 shows intensity and phase distributions of the input, measured linear propagation outputs, measured nonlinear propagation outputs, and back-propagation results for an object beam passing through a phase step sometimes referred to as a π-stripe.

FIG. 9 shows various panels 280 corresponding to intensities and phases (modulo 2π) of input (panels a and e) and outputs of the object beam 162 in linear propagation (panels b and f) and nonlinear propagation (panels c and g). Numerically reconstructed intensity and phase (panels d and h) of the input by back-propagation calculation are also shown. Where indicated, each scale bar represents approximately 50 µm. The dotted oval in panel g indicates appearance of π/2 discontinuity that is successfully eliminated in the reconstructed phase of panel h.

FIG. 9 further shows, in panel i, reconstruction cross-sections at various z values (indicated in panel j) using a backwards propagation algorithm of the internal dynamics of the dark stripe. Panel j shows simulation of evolution at the various z values indicated, with an example 5% simulated intensity noise. The shown scale bar represents approximately 50 µm.

In FIG. 9, such evolution for a dark stripe (generated by a π-shift phase discontinuity) is initially too narrow, for its intensity, to be a dark soliton. In the linear case (panel b), the stripe expands to roughly three times its original size. In the nonlinear case (panel c), the output stripe width has narrowed by ~30%. Numerical calculations show that this width coincides with the dark soliton width for the experimental parameters, but standard experimental techniques can say little about the beam dynamics. In other words, without showing invariant propagation, the existence of a soliton could not be proved.

As described herein, nonlinear digital holography can be used to reconstruct substantially the entire dynamics along the propagation path. As with the Gaussian beam case, one can reconstruct the input to yield reconstructed intensity and phase (panels d and h). Note that a phase defect at the nonlinear output (panel g) has been eliminated successfully in the reconstruction (panel h).

In panel i of FIG. 9, several cross-sections of the reconstruction, at intermediate distances within the crystal, are shown. As the beam propagates, the stripe widens to a dark soliton profile, radiating energy as it adjusts. The evolution is complex and can include the following effects: the initial noise smoothens, owing to the defocusing nonlinearity; the beam profile becomes more symmetric; diffraction of the central dark stripe is arrested; and the radiated waves selfsteepen and form dispersive shock waves. Similar profiles have been observed in fiber solitons, but to our knowledge have not been demonstrated in the spatial case. For example, two-dimensional (e.g., lateral XY) spatial profiles for two-dimensional imaging, in the context of some embodiments of the present disclosure, have not been demonstrated. Also, profiles associated with nonlinear propagation in unconfined space (sometimes referred to as free space) have not been demonstrated.

As described herein, substantially the entire dynamics is reconstructed, showing that the central profile settles into its dark soliton form at about 5 mm, whereas the tails need a longer propagation distance to relax. This semi-empirical reconstruction compares favorably with the ideal simulated case, shown in panel j.

As shown in FIGS. 6 and 7C, the back-propagation algorithm calibrated as described herein can be used to reconstruct an image of a pattern that is even more complex than the stripe pattern of FIG. 7B. As shown, the laser beam 158 passes through an Air Force 1951 resolution chart 240, producing a transmitted beam 242. The transmitted beam 242 is imaged with substantial unity magnification with a 4f system (244, 248) so as to yield an object beam 250 (162 in FIG. 6) to be propagated through the nonlinear medium 162 (FIG. 6). Reconstruction of the input based on the measured output is performed similarly as in the Gaussian case, by formatting the frames recorded by the camera (190) into 512×512 pixel frames.

Figure 10:
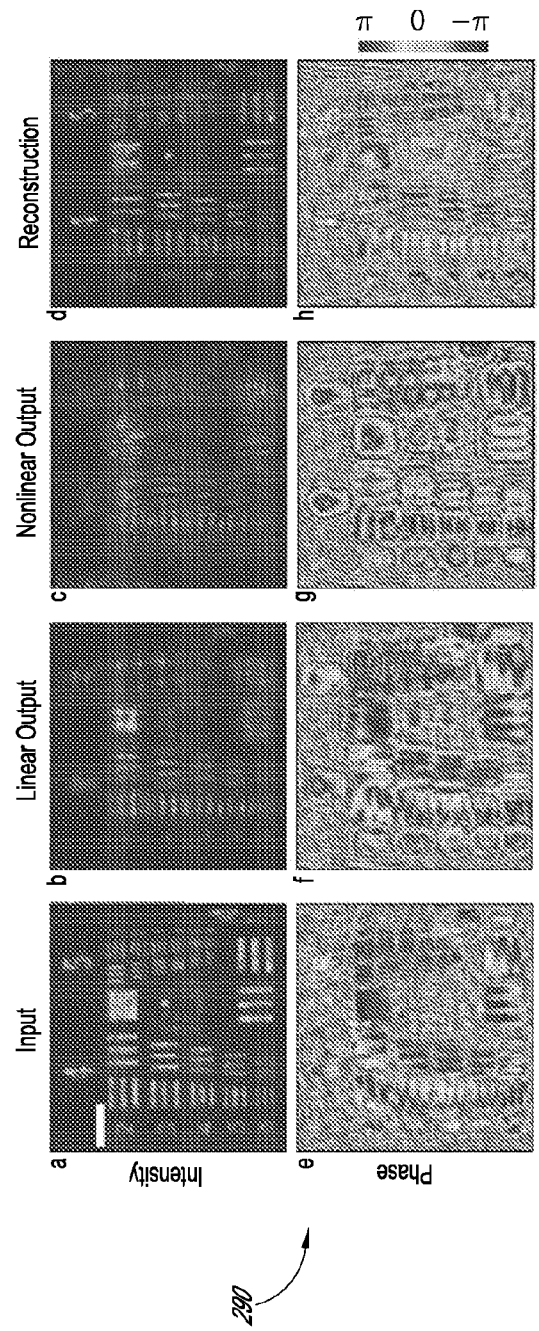
FIG. 10 shows intensity and phase distributions of the input, measured linear propagation outputs, measured nonlinear propagation outputs, and back-propagation results for an object comprising a more complicated USAF 1951 resolution chart.

FIG. 10 shows various panels 290 corresponding to intensities and phases (modulo 2π) of input (panels a and e) and outputs of the object beam 162 in linear propagation (panels b and f) and nonlinear propagation (panels c and g). Numerically reconstructed intensity and phase (panels d and h) of the input by back-propagation are also shown. Where indicated, each scale bar represents approximately 200 µm.

The Air Force 1951 resolution chart 240 is more complex than the stripe pattern and the Gaussian. In the linear case, the input (panels a and e) has diffracted considerably, as shown in panels b and f, but the characters are still recognizable. After nonlinear propagation (shown in panels c and g), however, the original intensity profile has been obliterated almost completely in the measured output, especially for the numerical symbols, and the phase profile is severely blurred. Nevertheless, there is very good agreement between experimental (panels a and e) and reconstructed phase and intensity (panels d and h) in the reconstructed image.

Based on the foregoing example with the complex Air Force 1951 resolution chart, there are a number of applications where image obliteration and image reconstruction can be implemented. For example, physical encryption of an image and/or information can be achieved using similar nonlinear propagation and reconstruction techniques. As with the dark soliton described in reference to FIG. 9, the reconstruction of the phase is particularly well defined. This is both surprising and fortunate, because the phase is typically a much more sensitive quantity and typically carries more information. Indeed, from the reconstructed phase of panel h, it is possible to resolve the 10 µm bars of the chart, a resolution limited mainly by the non-ideal properties (defects and striations) of the crystal.

As described herein in reference to FIGS. 6, 7A, 8A, and 8B, knowledge of an input and measurement of an output allows one to obtain one or more parameters that characterize a nonlinear medium through which the input propagates and becomes the output. In certain embodiments, such characterization of the nonlinear medium can be achieved by numerically back-propagating the measured output and reconstructing the input. Such reconstruction process can be an iterative process, where the input can be considered to be reconstructed when a given iteration yields an approximation that is sufficiently close to known input.

Figure 24:
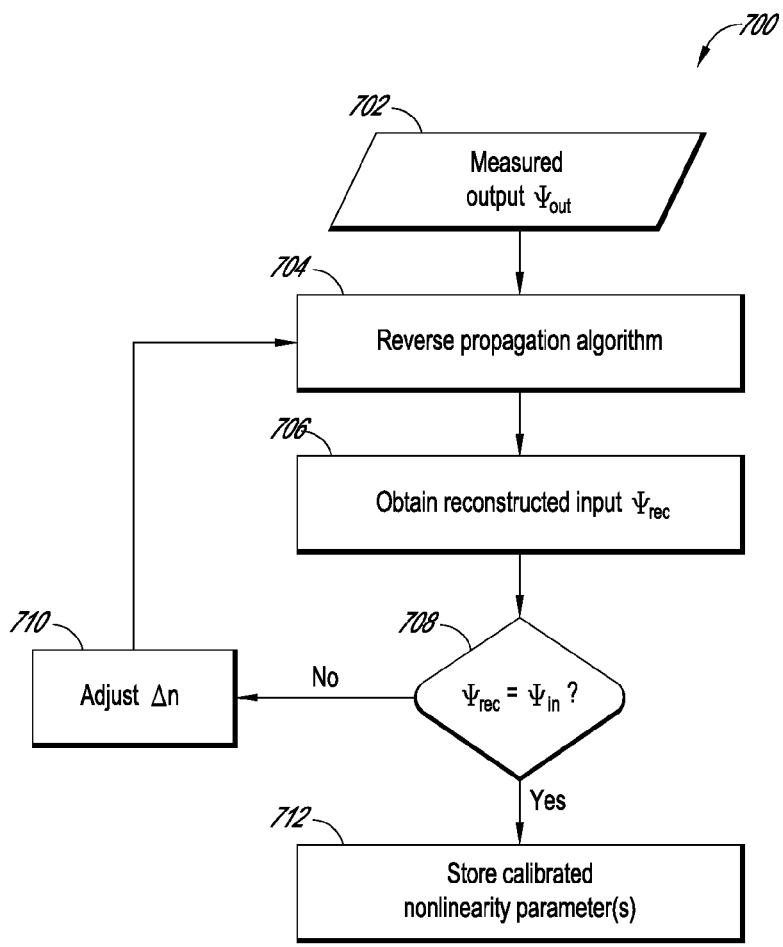
FIG. 24 shows an example algorithm that can be implemented to reconstruct an input wavefunction by an iterative back-propagation process.

FIG. 24 shows that in certain embodiments, an algorithm 700 can be implemented to perform such reconstruction of the input. As shown, an input for the algorithm 700 can include a measured output $\psi_{out}$. Such an input is provided to a block 704 where reverse propagation (or back-propagation) algorithm is performed. Such an algorithm can be based on Equation 3, where linear and nonlinear propagators successively evaluate (e.g., at $\Delta z$ intervals) an input along a direction that is reverse of the initial propagation direction of the input.

In block 706, a reconstructed input $\psi_{rec}$ is obtained from the reverse propagation algorithm 704. The reconstructed input $\psi_{rec}$ is then compared to the known input $\psi_{in}$; and in a decision block 708, the algorithm 700 determines whether the reconstruction ($\psi_{rec}$) is substantially equal to or sufficiently close to the input ($\psi_{in}$). If the answer is "No," then one or more nonlinearity parameters can be adjusted. For example, in block 710, the nonlinear index change $\Delta n$ (described herein in reference to Equations 1-3 and FIG. 6) can be adjusted, and the reverse propagation algorithm 704 can be repeated. If the answer is "Yes," then the one or more nonlinearity parameters that yielded the reconstruction ($\psi_{rec}$) can be stored.

In certain embodiments, such stored one or more parameters can be retrieved and utilized when the same or substantially same nonlinear medium is used to characterize an unknown input that yields a measured output. Similarly, the same nonlinearity parameter(s) can be retrieved and utilized for configuring an input that would yield a desired output when propagated through the nonlinear medium.

For example, in the situation where the unknown input is to be characterized based on the measured output, an algorithm similar to 700 (FIG. 24) can be implemented. As with algorithm 700, the measured output can be an input, and the reverse propagation algorithm 704 can numerically propagate the output to yield a reconstructed input. Because the nonlinear medium has already been characterized, the retrieved nonlinearity parameter(s) can be provided for the numerically propagation in the reverse propagation algorithm 704. The resulting reconstructed input is then taken to be an approximation of the unknown input.

In another example where an input is to be configured so that it would yield a desired output when propagated through the nonlinear medium, an algorithm similar to the foregoing reconstruction of the unknown input can be implemented. Here, the desired output can be treated similar to the measured output case; and the input can be determined in the same manner as the foregoing example (reconstructing an unknown input from a measured output).

Based on the foregoing measurement and reconstruction results and known properties of nonlinear propagation, there are some observations that can be made. The sharpness of the reconstruction (e.g., reconstruction for the complex Air Force 1951 resolution chart) highlights an irony inherent in self-defocusing media, where nonlinear mode-coupling of high spatial frequencies can lead to focusing effects. Although focusing nonlinearities can couple these modes, noise-induced instabilities can dominate the signal and may limit the ability to invert Equation 2.

Some non-limiting examples of beneficial end results that are or can be provided by various features of the present disclosure include larger effective numerical apertures and finer spatial resolution. Such capabilities can be achieved or implemented in various embodiments of digital imaging.

Figure 11:
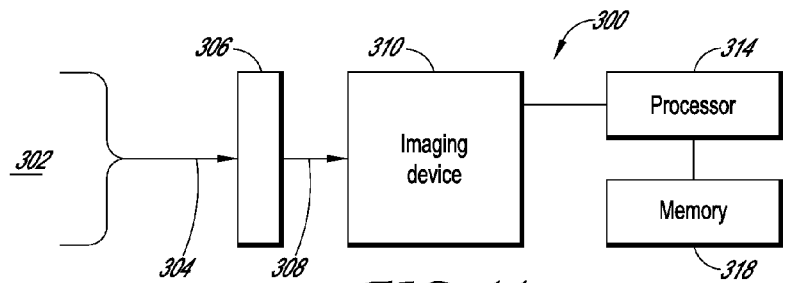
FIG. 11 shows that in certain embodiments, an imaging system can be configured to obtain an image of an object field through a nonlinear medium.

FIG. 11 shows a schematic depiction of an imaging configuration 300 where an input field 302 can be input (arrow 304) into a nonlinear medium 306 to yield an output field 308. An imaging device 310 is shown to form one or more images of the output field 308. Such one or more images can be processed by a processor 314 in communication with the imaging device 310 so as to characterize the input field 302.

As described herein, such characterization can be achieved by reconstructing the input field 302 via calculated back-propagation of the output field 308 through the nonlinear medium 306. In the imaging configuration 300 of FIG. 11, the nonlinear medium 306 can be one that has already been characterized. Thus, in certain embodiments, information about the nonlinear medium 306 can be stored in a computer-readable medium 318 so as to allow the processor 314 to perform the back-propagation algorithm. As described herein, the information about the nonlinear medium 306 can include one or more calibration parameters for the back-propagation algorithm.

In the imaging configuration of FIG. 11, measurement of an input is facilitated by its propagation through a nonlinear medium, followed by numerical back-propagation of a measured output through a model of the same nonlinear medium. Because the input is passed through the nonlinear medium, the nonlinear medium can facilitate recovery of information in the input that otherwise would be lost during propagation through a linear media.

Figure 12:
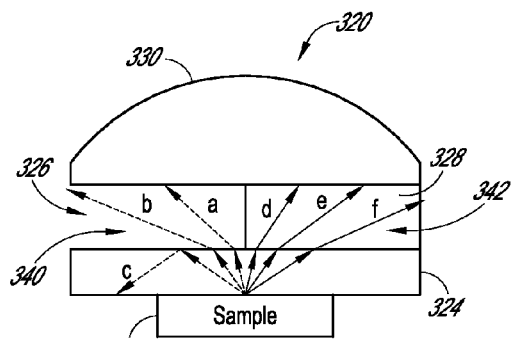
FIG. 12 shows a conventional microscope imaging configuration with various limitations imposed by numerical aperture.

As an example, FIG. 12 shows a microscope imaging configuration 320, where input rays from an object sample 322 pass through a slide cover 324 to further propagate to an objective lens 330 as rays generally indicated as 342. On the left side of the example configuration 320, an air gap 326 is provided between the slide cover 324 and the microscope objective lens 330. Accordingly, some of the rays passing through the slide cover 324 become lost, due to, for example, total internal reflection (e.g., ray indicated as "c"). Of the rays that emerge from the slide cover 324, some are directed so as to be accepted (e.g., ray "a") by the objective; while some escape the acceptance range (e.g., ray "b") of the objective due to, for example, difference in refractive indices between the slide cover 324 and the air gap 326, and the numerical aperture of the objective 330.

To mitigate at least some of such losses of input rays, some microscopes utilize immersion techniques, where a transmissive material having refractive index closer to the slide cover 324 is provided to fill the air gap. In FIG. 12, the transmissive material such as oil 328 is depicted as filling the gap between the slide cover 324 and the objective 330; and rays in the oil 328 are generally indicated as 342. Accordingly, loss due to internal reflection is reduced. For example, ray "f" that would have been lost by total internal reflection in the air-gap case is shown to be transmitted into the oil 328. Also, loss due to refraction beyond the numerical aperture of the objective is also reduced when compared to the air-gap case. For example, ray "e" that would have been lost by refraction beyond the numerical aperture of the objective in the air-gap case is shown to be accepted by the objective.

However, there still are rays that escape the acceptance range of the objective lens 330. For example, ray "f" is shown to be directed outside of the objective's acceptance range.

Figure 13A:
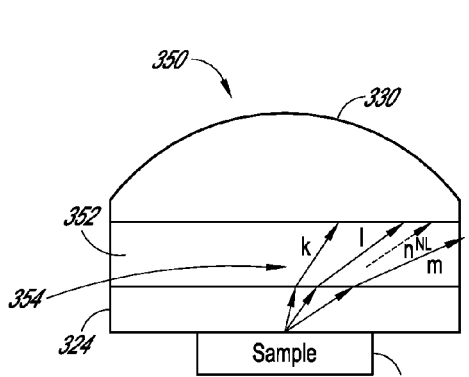
FIG. 13A shows an example microscopic imaging configuration where effective numerical aperture can be increased by use of a nonlinear medium.

FIG. 13A shows that in certain embodiments, a microscopic imaging configuration 350 can include a nonlinear medium 352 disposed between the object sample 322 and the objective lens 330. As shown, rays 354 indicated as "k," "l," and "m" emerge from the slide cover 324. Rays "k" and "l" are shown to propagate into the geometric acceptance range of the objective 330, while ray "m" escapes the range.

As is generally known, wave mixing can yield effects such as mode coupling and generation of daughter waves. Thus, in FIG. 13A, waves depicted as rays "l" and "m" can mix in the nonlinear medium 352 and generate a daughter wave or wave component indicated as "$n^{NL}$." Thus, while ray "m" is still not captured in the geometric acceptance range of the objective lens 330, information about ray "m" imparted to the daughter wave "$n^{NL}$" can be captured by acceptance of the daughter wave "$n^{NL}$."

Figure 13B:
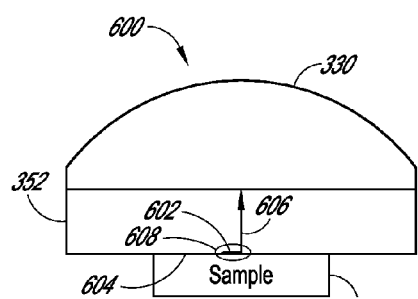
FIG. 13B shows an example microscope imaging configuration where information from an evanescent wave associated with a feature on a sample surface can be coupled with a wave transmitted through a nonlinear medium that is in contact with the sample surface.

FIG. 13B shows that in certain embodiments, a microscopic imaging configuration 600 can include a nonlinear medium 352 in contact with the object sample 322. As shown, an evanescent wave 602 representative of a feature (which may have a size less than a wavelength of light) on a surface 604 of the sample 322 can couple (depicted as 608) with a ray transmitted through the nonlinear medium 352 into the objective lens 330. In the example configuration 600, the portion of the surface 604 on which the feature (e.g., subwavelenth sized feature) is located is in contact with the nonlinear medium 352.

Figure 13C:
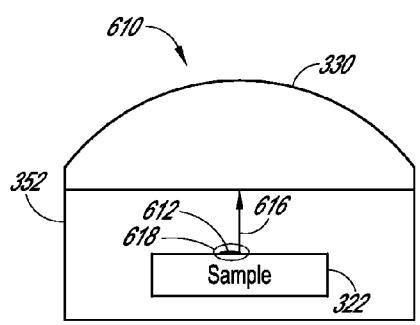
FIG. 13C shows an example microscope imaging configuration where information an evanescent wave associated with a feature on a sample can be coupled with a wave transmitted through a nonlinear medium where at least the feature on the sample is substantially embedded in the nonlinear medium.

FIG. 13C shows that in certain embodiments, a microscopic imaging configuration 610 can include a nonlinear medium 352 that at least partially encapsulates the object sample 322. In the example shown, the sample 322 is embedded in three dimensions within the nonlinear medium 352. Thus, evanescent waves (e.g., 612) corresponding to features (which may have a dimension less than a wavelength of light) on various surfaces of the sample 322 can couple (depicted as 618) with rays (e.g., 616) transmitted through at least a portion of the nonlinear medium 352 into the objective lens 330.

Thus, in certain embodiments, a super-resolution effect can result from knowledge of the nonlinear propagation kernel for the nonlinear medium 352. As described herein, such characterization of the nonlinear propagation allows reconstruction of the dynamics, deconvolution of the wave mixing, and therefore recovery of the underlying (missing) spatial features, thereby yielding better resolution of such features.

As described herein, in certain embodiments, this method can be applied to near-field, subwavelength reconstructions. In this case, nonlinear wave mixing couples evanescent waves or wave components with propagating ones. Evolution of such wave mixing and propagation in nonlinear media can be described by modifying the nonlinear Schrödinger equation (Equation 1) appropriately, and back-propagating a reverse solution as described herein. A relevant equation may be a full wave equation, including a full vector solution to Maxwell's equations, or any approximation thereof. Other methods can also be used.

In certain embodiments, this method has potential to work based on recent observations of the Goos-Hänchen effect (described in, for example, Goos, F. & Hänchen, H., *Ein newer and fundamentaler versuch zur totalreflexion*, Ann. Phys. 1, 333-346 (1947)), in which a totally internally reflected beam is spatially translated from the incident beam. This translation, owing to phase shifts of evanescent waves at the interface, is normally on the order of a wavelength but can be enhanced significantly by nonlinearity. Additional details concerning such effects and enhancements can be found at, for example, Artmann, K., *Berechnung der seitenversetzung des totalreflektierten strahles*, Ann. Phys. 2, 87-102 (1947); Tomlinson, W. J., Gordon, J. P., Smith, P. W. & Kaplan, A. E., *Reflection of a Gaussian beam at a nonlinear interface*, Appl. Opt. 21, 2041-2051 (1982); Emile, O., Galstyan, T., Le Floch, A. & Bretenaker, F, *Measurement of the nonlinear Goos-Hänchen effect for Gaussian optical beams*, Phys. Rev. Lett. 75, 1511-1513 (1995) and Jost, B. M., Al-Rashed, A.-A. R. & Saleh, B. E. A., *Observation of the Goos-Hänchen effect in a phase-conjugate mirror*, Phys. Rev. Lett. 81, 2233-2235 (1998). Combined with the reconstruction algorithm, this coupling of near-field behavior with far-field propagation can be extended to imaging in certain embodiments. Moreover, unlike traditional point-by-point scanning techniques, certain embodiments of the nonlinear digital holography disclosed herein include an inherently wide-angle, farfield form of microscopy.

From the opposite perspective, such nonlinear wave mixing could allow subwavelength lithography with super-wavelength-scale initial patterns. In certain embodiments, such an application of nonlinear wave mixing can be treated as a system 370 shown in FIG. 14. The system 370 includes a source 372 that provides a known input wave 374 that passes through a nonlinear medium 376 so as to yield a desired output wave 378. In certain embodiments, propagation properties in the medium 376, including nonlinear wave mixing, can be controlled based on knowledge of the nonlinear propagation. Thus, the input wave 374 can be configured accordingly so as to yield the desired output 378.

Similar to the example configuration described in reference to FIG. 11, information concerning the nonlinear propagation can be stored in a computer readable medium 390 in communication with a processor 380. The processor 380 can utilize such information and control the source to generate the configured input wave 374.

In certain embodiments, a lithographic device can include an arrangement of an optical element and a nonlinear medium similar to those in the microscope examples described in reference to FIGS. 13A-13C. Such a device can be operated in reverse so that an input configured based on a characterized nonlinear medium and passed through that nonlinear medium yields a desired output. Similar to the example advantages obtainable in the microscope, an effective numerical aperture of the device can be realized, thereby providing an increased resolution. Furthermore, evanescent wave interactions on a substrate (e.g., photoresist an/or semiconductor substrate) can be induced by the reversed process so as to allow, for example, formation of or interaction with subwavelength size features.

Figure 14:
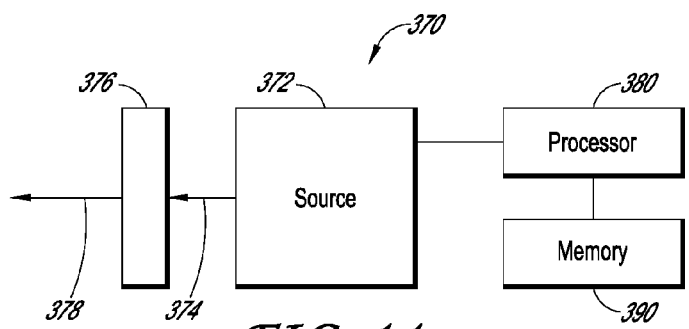
FIG. 14 shows that in certain embodiments, a system can be configured so that a desired output can be obtained by passing a configurable input through a characterized nonlinear medium.
Figure 15:
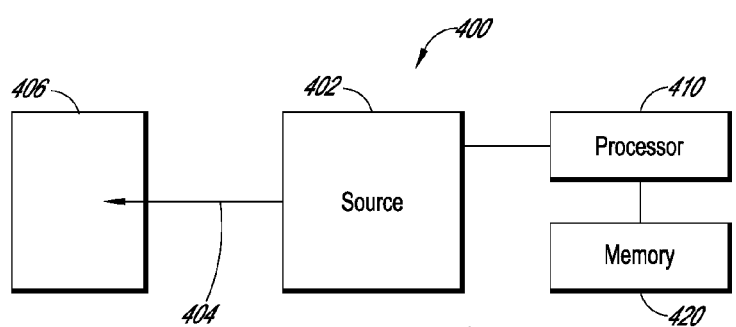
FIG. 15 shows that in certain embodiments, the system of FIG. 14 can be modified so that the desired output and corresponding effect of the output occurs within a characterized nonlinear medium.

In FIG. 14, the output wave 378 is depicted as emerging from the nonlinear medium 376. In certain situations, however, it may be desirable to generate and utilize results of nonlinear propagation in the nonlinear medium itself. Thus, in certain embodiments as shown in FIG. 15, a system 400 can include a source 402 that provides a known input wave 404 that enters a nonlinear medium 406. The entering wave begins to interact with the nonlinear medium 406, and such interaction can be characterized and controlled based on propagation properties stored in a computer readable medium 420 in communication with a processor 410. Thus, the input wave 404 can be configured to yield desired interaction in the nonlinear medium 406.

In certain embodiments, systems such as the example 400 shown in FIG. 15 can be utilized to achieve holographic recording and readout operations. By way of a non-limiting example, recording of information at different depths of media can be achieved. In certain embodiments, such recording medium can be the nonlinear medium 406, the source 402 can provide signals 404 representative of data records. Thus, recording to and reading from double or multiple layers of medium such as DVD (or similar optical medium) can be achieved. During such recording at a deeper layer, the intervening layer(s) may be affected by the recording beam. However, such interaction in the intervening layer(s) occurs in a known manner (which can be calculated by, for example, back-propagation method) as described herein, and can be compensated algorithmically during the write and/or readout process.

Within the foregoing recording and reading context, quality of signals associated with such operations can be improved by knowledge of the interactions occurring in the recording media. As described herein, such recording can be configured so as to yield a desired recording beam configuration. Such a configuration can include wave mixing to yield subwavelength recording capability with super-wavelength-scale beam, so as to yield a higher density recording.

In certain embodiments, a recording system described in reference to FIG. 15 can have components similar to those found in the lithographic system described herein. For example, a combination of a lens and nonlinear medium facilitates an increase in numerical aperture of the system and/or provides capability to induce evanescent wave based interactions for formation of subwavelength recording features.

Figure 16:
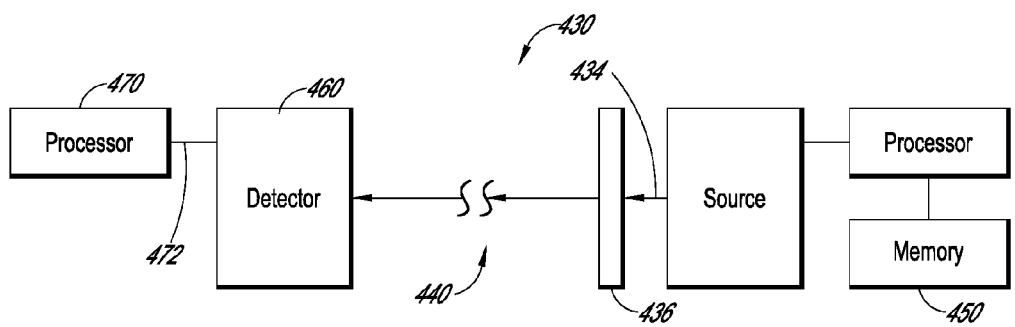
FIG. 16 shows that in certain embodiments, the system of FIG. 14 can be combined with a detection system for detecting the transmitted output and reconstructing the original input.

In certain embodiments, features associated with configurations where a desired output is obtained based on nonlinear propagation can be combined with features associated with configurations where an input is characterized, based again on nonlinear propagation. FIG. 16 shows an example system 430 where a desired output 440 is generated by propagation of an input 434 through a nonlinear medium 436 in a manner similar to that described in reference to FIG. 14. In certain embodiments, such output 440 can be propagated linearly to a remote location and be detected by a detector 460 under the control of a processor 470. The processor 470 can be provided with information concerning the nonlinear propagation (e.g., by having access to a computer readable medium 450), so as to allow reconstruction of the input 434.

In certain embodiments, the transmitted output 440 can be in a form suitable for reconstruction of an image. In certain embodiments, the transmitted output can be in a form that carries information that cannot be reconstructed without knowledge of the nonlinear propagation. Encryption and steganography are some non-limiting examples of possible applications.

Based on the present disclosure, it should be appreciated that various features can be applied to any situations where improved characterization of input or output waves is desirable. By way of non-limiting examples, some applications where nonlinear reconstruction and enhanced imaging can be applied include: enhanced field of view; improved depth determination; three-dimensional imaging via holography and nonlinear medium immersion; profilometry; tomography; edge detection; improved resolution; subwavelength resolution imaging; and improved axial resolution.

Additionally, various features of the present disclosure can be applied to material characterization wherever nonlinear propagation is involved. By way of non-limiting examples, such applications can include: nonlinear measurements to match model parameters; characterization of internal potentials, including those that are optically induced; identification and characterization of material defects; and identification and characterization of induced defects.

Additionally, various features of the present disclosure can be applied to provide improved sensitivity in certain optical applications. By way of non-limiting examples, such applications can include: amplification of features and correction of aberrations.

In the present disclosure, some of the examples are described in the context of coherent waves. For example, various observations associated with the setup 150 of FIG. 6 are in the context of coherent light such as a laser. It will be understood, however, that some or all of the features as described herein can also be applied to situations involving incoherent waves. For incoherent cases, correlation information can be obtained and incorporated appropriately in a known manner so as to allow, for example, numerical back-propagation an output to digitally reconstruct the incoherent input field. For such cases, known generalizations of the nonlinear Schrödinger equation (Equation 1) may be used, such as propagation of a mutual coherence function or radiation transport equations.

In various examples of the present disclosure, including the experimental setup described in reference to FIGS. 6-10, characterization of unknown inputs and configuring of desired outputs are described in the context of all-or-none presence or absence of a nonlinear medium. It will be appreciated, however, that similar techniques can also be implemented in situations where a propagation medium is characterized based on some difference in nonlinearity of the propagation medium. Such a difference can arise from, for example, differences in applied voltage, temperature, polarization, etc., or by use of a different nonlinear medium. In such a context, the all-or-none situation can be considered to be an example case of the nonlinearity-difference approach, where the "none" portion corresponds to substantially zero nonlinearity.

FIG. 17 shows a system 500 having a nonlinearity differential component 502 into which an input wave 504 (represented by a wavefunction $\psi_{in}$) is introduced. The input wave 504 propagates through the component 502 and emerges as an output wave 506 (represented by a wavefunction $\psi_{out}$).

In certain embodiments, such nonlinearity differential component can be characterized by a process 510 shown in FIG. 18. In a process block 512, a first output intensity distribution can be obtained with the nonlinearity differential component at first linearity. In a process block 514, a second output intensity distribution can be obtained with the nonlinearity differential component at second linearity. In a process block 516, complex output field can be obtained based on difference between the first and second output intensity distributions. In a process block 518, the complex output field thus obtained can be back-propagated through the medium having one of the first and second nonlinearities to reconstruct the input wavefunction. In a process block 520, the medium can be characterized based on the calculated back-propagation.

In certain embodiments, different output intensities—obtained from, for example, two or more different nonlinearities and/or differences between nonlinear and linear propagation—can be recorded; and full complex waveforms at the output can be reconstructed. As an example, output intensities can be measured after linear and nonlinear propagation, giving $I_{out}^{lin}=|\Psi_{out}^{lin}|^2$ and $I_{out}^{NL}=|\Psi_{out}^{NL}|^2$, respectively. A phase can be chosen $\Psi_{out}^{lin}$, after which the full wavefunction can be back-propagated to the input using a linear propagation algorithm so as to yield a reconstructed wavefunction $\Psi_{in}$. The reconstructed wavefunction $\Psi_{in}$ is then forward-propagated using a nonlinear propagation algorithm, creating a trial output wavefunction $\overline{\Psi}_{out}^{NL}$. The reconstructed amplitude of $\overline{\Psi}_{out}^{NL}$ is then replaced by the measured amplitude $\Psi_{out}^{NL}$. The process is then repeated: back-propagation with the nonlinear algorithm to reconstruct a wavefunction $\overline{\Psi}_{in}$, followed by forward-propagation with the linear algorithm to create $\overline{\Psi}_{out}^{lin}$. This is then replaced by the measured amplitude of $\Psi_{out}^{lin}$. This two-way reconstruction is then iterated until the unknown phase is recovered. Additional details about such phase retrieval algorithms can be found at, for example, Gerchberg, R. W. & Saxton, W. O., *A practical algorithm for the determination of the phase from image and diffraction plane pictures*, Optik 35, 237 (1972); and Fienup, J. R., *Phase retrieval algorithms: a comparison*, Appl. Opt. 21, 2758 (1982).

In situations involving incoherent light, there is an overall envelope phase, and other parameters such as correlation data can be utilized to characterize a statistical distribution representative of the incoherent light. These parameters are well known and described in such papers as Sun, C., Dylov, D. V., and Fleischer, J. W., *Nonlinear focusing and defocusing of partially coherent spatial beams*, Opt. Lett. 34, 3003 (2009). The foregoing phase retrieval and reconstruction method can be applied to the reconstruction of the incoherent light distribution as well.

In certain embodiments, the nonlinearity differential component 502 of FIG. 17 can be implemented in a number of ways. FIG. 19-21 show non-limiting example configurations where two or more nonlinearities can be provided.

In FIG. 19, an example configuration 530 includes a tunable nonlinear medium 532 whose nonlinear property can be adjusted by a controller 534. For example, application of different electrical potentials can yield different nonlinearities. As shown, an input wavefunction 536 can be provided at each of at least two nonlinearity settings to obtain at least two outputs 538.

In FIG. 20, an example configuration 540 includes two separate nonlinear media 542, 544. For the purpose of description herein, it will be assumed that the nonlinear media 542 and 544 have been characterized or are characterizable (for example, using methods described herein). An input 546 propagated through the first medium 542 yields a first output 548. The same input 546 propagated through the second medium 544 yields a second output 550.

In FIG. 21, an example configuration 640 includes a linear medium 642 and a nonlinear medium 644. An input 646 propagated through the linear medium 642 yields a first output 648. The same input 646 propagated through the nonlinear medium 644 yields a second output 650.

In certain embodiments, one or more features described in reference to FIGS. 17-21 can be implemented to obtain improved images, and/or to obtain desired outputs, in manners similar to those described in reference to FIGS. 11-16. By way of an example, FIG. 22 shows an imaging system 560 having an imaging device 568 that receives an output 566 of a nonlinearity difference component 564. The component 564 can be configured as described herein in reference to FIGS. 17-21 so as to receive an input wave 562 for two or more propagations therein. The imaging device 568 and/or the nonlinearity difference component 564 can be controlled by a processor 570; and such control can be facilitated by information about nonlinearities stored in a computer readable medium 572.

FIG. 23 shows a more specific example of the imaging system 560 of FIG. 22. A system 580 can include a camera whose field of view or numerical aperture is depicted as 584. In a first imaging operation, the camera 582 can obtain an image of without a nonlinear medium. Then, in a second imaging operation, the camera can obtain another image with an optical element 590 formed from a nonlinear medium. Intensity images obtained from the two operations can be combined to yield a complex field, and such a field can be back-propagated through the nonlinear medium so as to reconstruct the input associated with the second imaging operation.

As described herein, such reconstruction can yield information that would otherwise be absent. For example, information about waves outside of the field of view 584 can be retained by mixing of such waves and generation of nonlinear waves that survive and become part of the complex image. Thus, the nonlinear element 590 can provide an expanded field of view 592 for the camera 582.

In another example, information associated with fine or microscopic features in the input region that would otherwise be absent can be retained and transmitted by similar wave mixing. Thus, combined with the expanded field of view and/or numerical aperture feature(s), imaging via nonlinear element 590 can provide nonlinear digital images that are inherently wide-angle (e.g., expanded field of view and/or increased numerical aperture) and far field form of microscopy rich with fine details.

As described herein, some of the numerical propagation calculations are in the context of backward or reverse propagation. Such algorithms are used to describe, for example, reconstruction of an unknown input based on a measured output, or configuring an input based on a desired output. It will be understood, however, various features of the present disclosure can be implemented and/or achieved by numerical propagation calculations in a forward direction, where an output is constructed or reconstructed based on an input.

As described herein, some of the examples are in the context of electromagnetic radiation, and more particularly, in the context of light. It will be understood that various features of the present disclosure can be implemented and/or achieved in wave-related situations, including, for example, electromagnetic radiation outside of the light range and sound-related situations such as acoustics and ultrasonic applications.

In one or more example embodiments, the functions, methods, algorithms, techniques, and components described herein may be implemented in hardware, software, firmware (e.g., including code segments), or any combination thereof. If implemented in software, the functions may be stored on or transmitted over as one or more instructions or code on a computer-readable medium. Tables, data structures, formulas, and so forth may be stored on a computer-readable medium. Computer-readable media include both computer storage media and communication media including any medium that facilitates transfer of a computer program from one place to another. A storage medium may be any available medium that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

For a hardware implementation, one or more processing units at a transmitter and/or a receiver may be implemented within one or more computing devices including, but not limited to, application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a software implementation, the techniques described herein may be implemented with code segments (e.g., modules) that perform the functions described herein. The software codes may be stored in memory units and executed by processors. The memory unit may be implemented within the processor or external to the processor, in which case it can be communicatively coupled to the processor via various means as is known in the art. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Components may be added, removed, or rearranged; and method steps may be added, removed, or reordered. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method for characterizing a nonlinear medium, said method comprising:
providing a known input waveform to said nonlinear medium such that said input waveform propagates through said nonlinear medium, said input waveform representative of two or more dimensional spatial information;
characterizing an output waveform emerging from said nonlinear medium; and
computationally propagating said output waveform through said nonlinear medium so as to obtain an estimated waveform that sufficiently matches said input waveform, said computational propagation depending on one or more properties of said nonlinear medium such that obtaining of said estimated waveform results in characterization of said one or more properties of said nonlinear medium.

2. The method of claim 1, wherein said nonlinear medium comprises a nonlinear optical medium.

3. The method of claim 1, wherein said characterizing of said output waveform comprises characterizing a complex field emerging from said nonlinear medium.

4. The method of claim 3, wherein an amplitude is measured directly by an imaging device, and a phase is measured holographically by interference measurement.

5. The method of claim 3, wherein said input waveform comprises a coherent waveform.

6. The method of claim 3, further comprising measuring correlation among various components of said input waveform.

7. The method of claim 6, wherein said input waveform comprises an incoherent waveform.

8. The method of claim 1, wherein said computationally propagating comprises numerically evaluating a nonlinear wave equation applied to a field representative of said output waveform.

9. The method of claim 8, wherein said field comprises a slowly-varying scalar field.

10. The method of claim 8, wherein said numerically evaluating comprises numerically evaluating backward propagation of said scalar field through said nonlinear medium.

11. The method of claim 10, wherein said backward propagation of said field is based on said field being estimated as $\psi(z_i) \approx e^{-dz-N(\psi)} e^{-dz-D} \psi(z_f = z_i + dz)$, where quantity z represents a propagation direction with $z_f > z_i$, quantity dz represents an incremental propagation distance, and quantities D and N represent linear and nonlinear operators, respectively.

12. The method of claim 1, further comprising storing information about said one or more properties so as to allow retrieval and application to an unknown input waveform to characterize a resulting output waveform, or to a configurable input waveform that yields a desired output waveform.

13. An optical system, comprising:
a nonlinear optical medium configured to receive a first waveform and yield a second waveform;
a processor configured so as to obtain information about two of said nonlinear optical medium, first waveform, and second waveform and generate characterization of the remaining one of said nonlinear optical medium, first waveform, and second waveform, said generated characterization comprising numerical propagation of one of said first and second waveforms through said nonlinear optical medium.

14. The system of claim 13, wherein said processor is configured so as to obtain information about said first waveform and said second waveform and generate characterization of said nonlinear optical medium.

15. The system of claim 13, wherein said processor is configured so as to obtain information about said first waveform and said nonlinear optical medium and generate characterization of said second waveform.

16. The system of claim 15, wherein said second waveform comprises an output waveform emerging from said nonlinear optical medium.

17. The system of claim 16, wherein said output waveform includes one or more components originating from within said nonlinear optical medium as said first waveform propagates therethrough, such that when said output waveform is incident on a substrate, said one or more components interacts with said substrate.

18. The system of claim 17, wherein said one or more components are configured for use in lithography.

19. The system of claim 16, wherein said output waveform includes one or more components originating from within said nonlinear optical medium as said first waveform propagates therethrough, said one or more components having selected information attributable to said first waveform.

20. The system of claim 19, wherein said output waveform is configured for transmission to a remote location.

21. The system of claim 15, wherein said second waveform comprises a waveform at least partially within said nonlinear optical medium.

22. The system of claim 21, wherein said second waveform includes one or more components originating from within said nonlinear optical medium as said first waveform propagates through at least a portion of said nonlinear optical medium, such that said one or more components interacts with said nonlinear optical medium in a desired manner.

23. The system of claim 22, wherein said nonlinear optical medium comprises a data storage medium.

24. The system of claim 13, wherein said processor is configured so as to obtain information about said second waveform and said nonlinear optical medium and generate characterization of said first waveform.

25. The system of claim 24, wherein said first waveform comprises a first component and a second component, said first and second components coupling in said nonlinear optical medium to generate a new nonlinear component that becomes part of said second waveform even if either or both of said first and second components of said first waveform do not become part of said second waveform, said new nonlinear component carrying information imparted to it during said coupling.

26. The system of claim 25, wherein at least one of said first and second components of said first waveform comprises an evanescent wave component associated with an object being observed.

27. The system of claim 26, wherein said evanescent wave is associated with a subwavelength sized feature on said object.

28. The system of claim 26, wherein said object is in contact with said nonlinear optical medium so as to allow coupling of said evanescent wave component with one of said first and second components so as to yield said new nonlinear component.

29. The system of claim 28, wherein said nonlinear optical medium is part of a sample holder for holding said object.

30. The system of claim 29, wherein said sample holder comprises a microscope slide.

31. The system of claim 29, wherein said sample holder comprises an enclosure that encloses at least a portion of said object being imaged.

32. The system of claim 25, wherein at least one of said first and second components of said first waveform comprises a peripheral component that would be lost and not become part of said second waveform if propagated through a linear optical medium.

33. The system of claim 32, wherein said information imparted by said peripheral component to said new nonlinear component increases effective field of view said first waveform captured by said second waveform.

34. The system of claim 33, wherein said nonlinear optical medium comprises a filter configured to be placed in front of an imaging device so as to provide said increased effective field of view.

35. A profilometry device comprising the optical system of claim 13.

36. A tomography device comprising the optical system of claim 13.

37. A material testing device comprising the optical system of claim 13.

38. The device of claim 37, wherein said optical system is configured to characterize internal potentials of a material being tested.

39. The device of claim 37, wherein said optical system is configured to identify and characterize material defects or induced defects of a material being tested.

40. A computer-readable medium containing machine-executable instructions that, if executed by a device having one or more processors, causes the device to perform operations comprising:

obtaining a digital representation of a measured output waveform resulting from propagation of an input waveform through a nonlinear medium; and computationally propagating said digital representation of said measured output waveform through said nonlinear medium so as to reconstruct a digital representation of said input waveform, said computational propagation depending on one or more properties of said nonlinear medium, information about said one or more properties stored in said computer-readable medium or accessible by said machine-executable instructions.

41. A method for characterizing nonlinear wave propagation, said method comprising:

providing a known input waveform to propagate through a first nonlinear environment so as to yield a first intensity distribution;

providing said known input waveform to propagate through a second nonlinear environment so as to yield a second intensity distribution;

determining an output waveform based at least in part on a difference between said first and second intensity distributions; and computationally propagating said output waveform through one of said first and second nonlinear environments to reconstruct an approximation of said input waveform.

42. The method of claim 41, further comprising characterizing said one of said first and second nonlinear environments based on said computational propagation.

43. The method of claim 42, further comprising storing information representative of said characterization of said one of said first and second nonlinear environments in a computer-readable medium.

44. The method of claim 41, wherein said nonlinear wave propagation comprises nonlinear propagation of electromagnetic radiation.

45. An optical system, comprising:

a nonlinearity component configured to provide first and second nonlinear propagation environments for an input waveform to respectively yield first and second output waveforms;

an imaging device configured to detect at least intensity portions of said first and second output waveforms and generate first and second intensity distributions, respectively; and a processor configured to determine an output waveform based at least in part on a difference between said first and second intensity distributions.

46. The system of claim 45, wherein said processor is further configured to computationally propagate said output waveform through one of said first and second nonlinear propagation environments to reconstruct an approximation of said input waveform.

47. The system of claim 46, wherein said nonlinearity component comprises a first medium and a second medium, said first medium providing said first nonlinear propagation environment and said second medium providing said second nonlinear propagation environment.

48. The system of claim 47, wherein one of said first and second environment comprises a propagation medium having a substantially zero degree of nonlinearity.

49. The system of claim 45, wherein said nonlinearity component comprises a tunable nonlinear medium and a controller, said controller configured to provide at least two settings for said tunable nonlinear medium so as to provide said first and second nonlinear propagation environments.

50. The system of claim 45, wherein said output waveform includes phase information retrieved from said difference between said first and second intensity distributions.

51. The system of claim 45, wherein said output waveform includes polarization information retrieved from said difference between said first and second intensity distributions.

52. The system of claim 45, wherein said input waveform comprises incoherent wave, and wherein said output waveform includes correlation information to accommodate said incoherent wave.

53. An apparatus, comprising:
  a nonlinear element configured so as to provide a nonlinear propagation environment for a wave passing therethrough, said nonlinear element dimensioned to receive an input and yield an output; and
  a computer-readable medium containing instructions that calculates one of said input and output if given the other, said calculation achieved numerically in an iterative manner using one or more parameters that characterize said nonlinear propagation environment.

54. The apparatus of claim 53, wherein said apparatus comprises an imaging device.

55. The apparatus of claim 54, wherein said instructions calculates said input based on said output.

56. The apparatus of claim 55, wherein said output comprises a measured output.

57. The apparatus of claim 56, wherein said apparatus comprises a microscope.

58. The apparatus of claim 55, wherein said output comprises a desirable output.

59. The apparatus of claim 58, wherein said apparatus comprises a lithographic device.

* * * * *